US012667554B1

(12) United States Patent
Gande et al.

(10) Patent No.: US 12,667,554 B1
(45) Date of Patent: Jun. 30, 2026

(54) ORAL SOLID CHLORTHALIDONE COMPOSITIONS

(71) Applicant: Ingenus Pharmaceuticals, LLC, Orlando, FL (US)

(72) Inventors: Mukteeshwar Gande, Monroe, NJ (US); Praveen Reddy Billa, Flanders, NJ (US); Jagatpal Reddy Surikanti, Parsippany, NJ (US)

(73) Assignee: Ingenus Pharmaceuticals, LLC, Orlando, FL (US)

( * ) Notice: Subject to any disclaimer, the term of this patent is extended or adjusted under 35 U.S.C. 154(b) by 0 days.

(21) Appl. No.: 19/319,380

(22) Filed: Sep. 4, 2025

(51) Int. Cl.
*A61K 31/4035* (2006.01)
*A61K 9/20* (2006.01)

(52) U.S. Cl.
CPC ........ *A61K 31/4035* (2013.01); *A61K 9/2009* (2013.01); *A61K 9/2013* (2013.01); *A61K 9/2054* (2013.01); *A61K 9/2059* (2013.01); *A61K 9/2095* (2013.01)

(58) Field of Classification Search
CPC ..... A61K 9/00; A61K 9/2054; A61K 31/4035
See application file for complete search history.

(56) References Cited

U.S. PATENT DOCUMENTS

| | | | | |
|---|---|---|---|---|
| 8,288,394 | B2 * | 10/2012 | Duran Lopez | ....... C07D 403/06 544/333 |
| 9,387,249 | B2 * | 7/2016 | Kupfer | ................... A61K 31/41 |
| 11,957,658 | B2 | 4/2024 | Jagadale et al. | |

FOREIGN PATENT DOCUMENTS

| | | | |
|---|---|---|---|
| EP | 2582361 B1 | 9/2014 | |
| WO | 2005014043 A1 | 2/2005 | |
| WO | 2018084627 A2 | 5/2018 | |
| WO | WO-2020041864 A1 * | 3/2020 | ............... A61P 9/12 |

OTHER PUBLICATIONS

N.G. Raghavendra Rao et al. Design of fast dissolving tablets of chlorthalidone using novel co-processed superdisintegrants, J Chem. Pharm. Res. 2, 671-679. (Year: 2010).*

G.C. Ceschel et al. Optimization of a tablet containing chlorthalidone, Drug Development and Industrial Pharmacy, 25, 1167-1176. (Year: 1999).*

Narurkar et al., "Effect of Particle Size on the Dissolution Characteristics of Chlorthalidone", Drug development and industrial pharmacy, 13(2), 319-328 (1987).

Dangree et al., "Formulation and development of solid self micro-emulsifying drug delivery system (S-SMEDDS) containing chlorthalidone for improvement of dissolution", Journal of Pharmaceutical Investigation (2016), 46(7), 633-644.

* cited by examiner

*Primary Examiner* — Michael G. Hartley
*Assistant Examiner* — Jagadishwar R Samala
(74) *Attorney, Agent, or Firm* — The Belles Group, P.C.

(57) ABSTRACT

Described herein are solid oral compositions comprising chlorthalidone, or a pharmaceutically acceptable salt thereof; and a pharmaceutically acceptable excipient, wherein the chlorthalidone has a Sauter mean diameter ranging from about 8 μm to about 14 μm. Methods of making and using these compositions are also described herein.

12 Claims, No Drawings

ORAL SOLID CHLORTHALIDONE COMPOSITIONS

FIELD OF THE DISCLOSURE

The present disclosure relates to solid oral compositions comprising chlorthalidone, or a pharmaceutically acceptable salt thereof, with defined particle characteristics, and methods for its preparation. More specifically, the disclosure pertains to a rapidly disintegrating, stable tablet formulations of chlorthalidone, useful in the treatment of hypertension and related cardiovascular conditions.

BACKGROUND

Chlorthalidone is a thiazide-like diuretic widely used in the management of hypertension and fluid retention associated with congestive heart failure and renal disorders. Commercially available formulations suffer from challenges related to poor solubility, slow disintegration, and chemical instability over long-term storage.

Chlorthalidone poses several formulation and bioavailability challenges due to its physicochemical characteristics. One of the primary issues is its poor aqueous solubility, which significantly limits the drug's dissolution rate in gastrointestinal fluids. This slow dissolution delays absorption, resulting in reduced and variable bioavailability among patients. In addition to solubility issues, chlorthalidone tends to form large and irregular crystalline particles that are hydrophobic in nature. This morphology reduces surface area and hinders effective wetting, leading to poor dispersion and dissolution during oral administration. Therefore, inconsistency in particle morphology or size can directly affect the uniformity and performance of the final dosage form.

Further, when chlorthalidone is administered in low doses such as 12.5 mg per tablet, content uniformity is a critical concern. Low-dose drugs are inherently difficult to formulate as the active pharmaceutical ingredient must be uniformly distributed within a much larger volume of excipients. Minor inconsistencies in blending or particle size can result in non-uniform tablets and dosage variability. The low wettability of chlorthalidone also complicates blending during formulation, particularly for low-dose tablets, where uniform drug distribution is critical.

Accordingly, there exists a need for an improved chlorthalidone formulation that ensures rapid drug release, specific particle characteristics, high stability, and robust processability through direct compression techniques. However, it is also challenging to achieve the optimum particle characteristics, as under-micronized particles result in poor dissolution properties and micronized particles possess handling challenges during manufacturing. In view of these shortcomings related to poor solubility, there is need for novel and effective formulations of chlorthalidone which include selective particle characteristics having a balance of finer and coarser particle across the range, while offering manufacturability and stability suitable for commercial pharmaceutical applications.

Both solubility and the process of dissolution are governed by surface phenomena. In the context of poorly water-soluble drug substances, the rate and extent of dissolution are critically dependent on the available surface area of the drug particles exposed to the dissolution medium. While particle size distribution (PSD) is commonly used to characterize particulate systems, it alone does not inherently reflect the surface area available for dissolution, whereas Sauter's mean diameter being surface area-weighted, is more directly related to dissolution rate because dissolution is a surface phenomenon.

Sauter Mean Diameter is the average particle size based on surface area and volume. This ratio is very useful when surface processes are important. It characterizes a particle system in terms of its surface area per unit volume, which is particularly important in processes involving mass transfer such as dissolution of BCS class IV drugs.

Certain embodiments of the present invention are designed to address the foregoing challenges.

SUMMARY

Chlorthalidone presents significant formulation and bioavailability challenges due to its poor aqueous solubility, low gastrointestinal permeability as being a BCS Class IV drug. These properties result in slow dissolution, variable absorption, and inconsistent therapeutic response. Particle characteristics greatly influence dissolution; and hence, must be carefully controlled as excessive size reduction results in powder handling and static electricity challenges thereby increasing processing complexity of using fluidized air mills for particle size reduction.

Therefore, by optimizing and controlling Sauter's ratio $(D_{3,2})$, embodiments of the present invention ensure an optimum surface area per unit volume which provides the desired dissolution kinetics. The Sauter's mean diameter provides a holistic metric that captures the functional impact of particle morphology on dissolution behavior.

Some embodiments of the present invention provide a solid oral composition comprising chlorthalidone or a pharmaceutically acceptable salt thereof, having the desired Sauter's mean diameter $(D_{3,2})$ range and specific surface area, thereby avoiding significant batch-to-batch variability in dissolution kinetics. Other embodiments of the present invention provide a composition comprising chlorthalidone, or a pharmaceutically acceptable salt thereof, having a desired a particle characteristic such that the composition is capable of releasing chlorthalidone in a timely manner in a dissolution media according to USP method tested at different pH values between 1.2 to 6.8, thereby consistently providing chlorthalidone for absorption throughout the gastrointestinal tract without significant variation. Yet other embodiments of the present invention provide a process for manufacturing a composition comprising chlorthalidone or a pharmaceutically acceptable salt thereof, having the desired particle parameters.

Still further embodiments of the present invention provide a method of treating a patient having hypertension through administration of a composition comprising chlorthalidone having specific particle characteristics.

In some embodiments, the present invention provides a solid oral composition of chlorthalidone or a pharmaceutically acceptable salt thereof, having a specific Sauter's mean diameter $(D_{3,2})$ range and the specific surface area which significantly improves dissolution rate, stability, and content uniformity. Sauter's mean diameter captures the contribution of finer particles more effectively than average particle size, making it a better predictor of dissolution performance. Although, average particle size might still be monitored for consistency, Sauter's mean diameter is more sensitive to changes in the fine particle fraction, which is critical for dissolution.

In other embodiments, the present invention provides a solid oral composition comprising: chlorthalidone, or a pharmaceutically acceptable salt thereof, having a Sauter's mean diameter ($D_{3,2}$) of from about 8 μm to about 14 μm; and a pharmaceutically acceptable carrier comprising an excipient selected from: a diluent; a disintegrant; a glidant; a lubricant; and a combination of two or more thereof.

Further embodiments of the present invention provide a solid oral composition comprising chlorthalidone with controlled particle characteristics, wherein the composition exhibits timely release of chlorthalidone in dissolution media across a pH range (pH 1.2 to pH 6.8), when tested in accordance with the USP Type I (basket) apparatus. This ensures uniform availability of the drug for absorption throughout the gastrointestinal tract and reduces variability to a greater extent.

Still further embodiments of the present invention provide a solid oral composition comprising: chlorthalidone as a pharmaceutically active ingredient having, a Sauter's mean diameter ($D_{3,2}$) from about 8 μm to about 14 μm; and pharmaceutically acceptable excipient selected from group consisting of a diluent, a disintegrant, a glidant, a lubricant or a mixture thereof; wherein the composition releases not less than about 58% of the chlorthalidone within 15 minutes in dissolution media having a pH of 1.2, 4.5, or 6.8; and wherein the dissolution testing is conducted in a USP Type I (basket) apparatus at 100 rpm in 500 ml of dissolution media maintained at 37±0.5° C.

In some embodiments, the present invention provides a solid oral composition comprising: chlorthalidone, or a pharmaceutically acceptable salt thereof, having: (a) a Sauter's mean diameter ($D_{3,2}$) from about 8 μm to about 14 μm; and (b) a specific surface area from about 0.25 m²/g to about 1 m²/g; and a pharmaceutically acceptable carrier comprising an excipient selected from: a diluent; a disintegrant; a glidant; a lubricant; and a combination of two or more thereof, wherein the composition releases not less than about 58% of the chlorthalidone within 15 minutes in dissolution media having a pH of 1.2, 4.5, or 6.8; and wherein the dissolution testing is conducted in a USP Type I (basket) apparatus at 100 rpm in 500 ml of dissolution media maintained at 37±0.5° C.

In addition to the desired dissolution profile, the optimization of particle parameters provides enough chemical and physical stability to the composition when tested for long term conditions as well as accelerated conditions.

In some embodiments, the present invention provide a solid oral composition comprising: chlorthalidone, or a pharmaceutically acceptable salt thereof, having a Sauter's mean diameter ($D_{3,2}$) of from about 8 μm to about 14 μm; and a pharmaceutically acceptable carrier comprising an excipient selected from: a diluent; a disintegrant; a glidant; a lubricant; and a combination of two or more thereof; wherein the composition releases not less than about 58% of the chlorthalidone within 15 minutes in dissolution media having a pH of 1.2, 4.5, or 6.8; wherein the dissolution testing is conducted in a USP Type I (basket) apparatus at 100 rpm in 500 ml of dissolution media maintained at 37±0.5° C.; and wherein the composition after storage at 25° C. and 60% RH for at least 12 months, or after storage at 40° C. and 75% relative humidity for 6 months has at least two of (a) to (c):

i. the total impurities in an amount that does not exceed about 1%;

ii. impurity B in an amount that does not exceed about 0.5%;

iii. chlorthalidone ethyl ether impurity in an amount that does not exceed about 0.1%;

wherein the impurity concentrations are calculated based on the weight of chlorthalidone.

In further embodiments, the inventive compositions of the present invention after storage at 25° C. and 60% RH for at least 12 months, or after storage at 40° C. and 75% RH for 6 months has (a) to (c):

(a) the total impurities in an amount that does not exceed about 1%;

(b) impurity B in an amount that does not exceed about 0.5%;

(c) chlorthalidone ethyl ether impurity in an amount that does not exceed about 0.1%;

wherein the impurity concentrations are calculated based on the weight of chlorthalidone.

In other embodiments, a composition of the present invention is stored at 25° C. and 60% RH and has at least two of (a) to (c) after at least 24 months or at least 36 months. In further embodiments, the composition is stored at 25° C. and 60% RH and has (a) to (c) after at least 24 months or at least 36 months.

Although particle size reduction via milling is a known and widely applied technique, it cannot be the sole focus when aiming to enhance dissolution performance across different pH media along with ease of manufacturing such as handling of powders. Instead, emphasis has been placed on the selection and engineering of particles with appropriate characteristics, including the optimal combination of fine and coarse fractions that collectively contribute to a favorable surface area profile. Such a strategically optimized approach enables better control over surface-driven properties such as wettability and dispersion, which are critical for achieving consistent and desired dissolution of the drug. Certain embodiments of the present invention provide a process wherein the desired particle characteristics are achieved and used to manufacture the inventive compositions, thereby achieving the desired dissolution of a poorly soluble drug such as chlorthalidone.

In some embodiments, the present invention also provides a process for manufacturing an oral solid composition having a desired particle parameters of chlorthalidone as an active ingredient. The process includes milling which plays a crucial role in the formulation of poorly soluble drugs like chlorthalidone by reducing particle size and increasing surface area, which significantly enhances the dissolution rate. For low-dose formulations, achieving a uniform and narrow particle size distribution through controlled milling improves blend uniformity and ensures consistent drug content in each dosage unit. Additionally, optimized milling prevents over-micronization, which can lead to instability, aggregation, or degradation due to increased surface energy. Properly milled particles also exhibit better flow and compressibility, facilitating efficient manufacturing processes such as direct compression. Therefore, precise control of the milling parameters is essential to improve the solubility, stability, and manufacturability of poorly soluble active pharmaceutical ingredients, such as chlorthalidone.

In some embodiments, the present invention provides a solid oral composition comprising: chlorthalidone, or a pharmaceutically acceptable salt thereof, having a Sauter's mean diameter ($D_{3,2}$) of from about 8 μm to about 14 μm; and a pharmaceutically acceptable carrier comprising an excipient selected from: a diluent; a disintegrant; a glidant; a lubricant; and a combination of two or more thereof; wherein the composition releases not less than about 58% of the chlorthalidone within 15 minutes in dissolution media having a pH of 1.2, 4.5, or 6.8; wherein the dissolution testing is conducted in a USP Type I (basket) apparatus at 100 rpm in 500 ml of dissolution media maintained at 37±0.5° C.; and wherein the solid oral composition is prepared by the method comprising:

(a) passing chlorthalidone through Fitz-mill using a 0.020" screen, with knives in reverse position, at a high speed of approximately 4700 rpm at a feed rate of approximately 150 g/minute and re-milling the material under the same conditions to provide chlorthalidone having the Sauter's mean diameter ($D_{3,2}$) from about 8 μm to about 14 μm;

(b) sifting sodium starch glycolate, a portion of colloidal silicon dioxide, and pregelatinized starch through sieve #20;

(c) premixing microcrystalline cellulose in a V-blender at approximately 21 rpm for about 4 minutes;

(d) blending the milled chlorthalidone from step (a) and sifted materials from step (b) with the premixed microcrystalline cellulose from step (c) in a V-blender at 21 rpm for about 4 minutes to form a blend;

(e) sifting the blend obtained in step (d) through Sieve #30;

(f) blending the sifted blend of step (e) for about 13 minutes at 21 rpm in a V-blender;

(g) sifting a remaining portion of colloidal silicon dioxide through Sieve #20 using a suitable portion of the step (f) blend to aid in mixing and screening;

(h) blending the sifted second portion of colloidal silicon dioxide of step (g) blend in a V-blender of step (f) for about 7 minutes at 21 rpm;

(i) sifting calcium stearate through sieve #40 using a portion of the step (h) blend to aid in mixing and screening;

(j) blending the calcium stearate with the blend from step (i) in a V-blender from step (h) for about 7 minutes at 21 rpm to obtain a final mix blend;

(k) compressing the final-mix blend into one or tablets using a direct compression tablet press; and (l) packaging the tablets into high-density polyethylene (HDPE) containers.

In some embodiments, the present invention provides a method of treating hypertension and/or lowering blood pressure in a subject in need thereof, comprising administering a composition having chlorthalidone having a particular particle characteristic so that it uniformly releases drug and thereby making drug bioavailable without erratic absorption in GIT.

In other embodiments, the present invention provides a method of treating a subject having hypertension and to lower blood pressure in need thereof, comprising administration of solid oral composition comprising chlorthalidone and pharmaceutically acceptable excipients.

In certain embodiments, the present invention provides a method of treating, reducing, preventing or ameliorating a symptom associated with hypertension in a subject in need thereof, comprising administering to said subject in need thereof, an effective amount of a solid oral composition comprising:

chlorthalidone, or a pharmaceutically acceptable salt thereof, having a Sauter's mean diameter ($D_{3,2}$) of from about 8 μm to about 14 μm; and a pharmaceutically acceptable carrier comprising an excipient selected from: a diluent; a disintegrant; a glidant; a lubricant; and a combination of two or more thereof;

wherein the composition releases not less than about 58% of the chlorthalidone within 15 minutes in dissolution media having a pH of 1.2, 4.5, or 6.8; and wherein the dissolution testing is conducted in a USP Type I (basket) apparatus at 100 rpm in 500 ml of dissolution media maintained at 37±0.5° C.

In further embodiments, the solid oral composition is in the form of a tablet which is unscored and administered to a subject in need thereof, as a whole without splitting.

For administration of a low dose of chlorthalidone to a patient in need thereof, it is usual practice to divide or split the unscored chlorthalidone tablet having higher dose into the small dose as per the requirement. However, such practices pose a risk of not delivering an accurate dose to a patient since the splitting of an unscored tablet generally leads to an uneven dose.

In some embodiments, the present invention provides a method of treating, reducing, preventing or ameliorating a symptom associated with hypertension in a subject in need thereof, comprising administering to said subject in need thereof, an effective amount of a tablet comprising chlorthalidone, or a pharmaceutically acceptable salt thereof, which need not be split or divided before administration. In other embodiments, the present invention provides a method of treating, reducing, preventing or ameliorating a symptom associated with hypertension in a subject in need thereof, comprising administering to said subject in need thereof, an effective amount of a tablet comprising chlorthalidone, or a pharmaceutically acceptable salt thereof, which facilitates the use of a dosage unit of 12.5 mg or multiple of 12.5 mg dosage unit required, wherein the administration to the subject does not require any splitting of the dosage form.

DETAILED DESCRIPTION

As used in the specification and the appended claims, the singular forms of "a," "an" and "the" include plural references unless the context clearly dictates otherwise.

As used herein, the term "about" refers to the deviation of +5% from the said value. For example, about 55% encompasses both the values as 55%+5% and 55%-5%.

As used herein, the term "chlorthalidone" includes solvates, hydrates, anhydrates, enantiomers, isomers, polymorphs, or mixture thereof. In one embodiment, the active ingredient is chlorthalidone, which is either crystalline or amorphous in physical form. In one embodiment, the active ingredient is chlorthalidone, which is in hydrate or anhydrate form. In one embodiment, the solid oral composition includes chlorthalidone in crystalline form I.

As used herein, the term "pharmaceutically acceptable salts" refers pharmaceutically acceptable salts of compound, including acid addition salts and base salts formed by reaction with suitable inorganic or organic acids or bases. Such salts include, but are not limited to, salts with hydrochloric, hydrobromic, sulfuric, phosphoric, acetic, citric, fumaric, maleic, tartaric, methanesulfonic, and benzenesulfonic acids, or with bases such as sodium, potassium, calcium, magnesium, ammonia, or organic amines (e.g., ethanolamine, triethylamine, N-methylglucamine). The term also includes solvates (e.g., hydrates), zwitterionic forms, and any polymorphic or crystalline forms thereof, provided they are pharmaceutically acceptable.

As used herein, the term "active ingredient" or "active pharmaceutical ingredient (API)" or "pharmaceutically active ingredient" refers to a pharmaceutically acceptable substance or compound that provides a therapeutic, prophylactic, diagnostic, or physiological effect when administered to a subject. The active ingredient is responsible, at least in part, for the desired biological or pharmacological activity of the pharmaceutical composition. The active ingredient may be present in combination with one or more pharmaceutically acceptable carriers, excipients, or other active or inactive components. In one embodiment, the present invention provides a solid oral pharmaceutical composition comprising chlorthalidone as a pharmaceutically active ingredient.

As used herein, the term "milled API" or 'milled chlorthalidone" refers to chlorthalidone that has undergone a particle size reduction process, such as mechanical milling, micronization, or other suitable comminution techniques, to produce particles of desired parameters. In one embodiment, the milled API or milled chlorthalidone of the present invention has a Sauter's mean diameter from about 7 $\mu$m to 15 $\mu$m or from about 8 $\mu$m to 14 $\mu$m. Milled APIs exhibits altered physical properties, such as increased surface area, improved solubility an dissolution rate, which contribute to the performance of the pharmaceutical composition. Unless otherwise specified, the milled API is prepared by both dry and wet milling processes which includes jet milling, ball milling, hammer milling, Fitz milling or any other pharmaceutically acceptable milling techniques.

As used herein, the term "the Sauter's mean diameter" or "$D_{(3,2)}$" or "surface area-weighted mean diameter" refers to mean particle diameter, which represents the diameter of a sphere having the same volume-to-surface area ratio as the entire particle sample, calculated as the ratio of the sum of the cubes of particle diameters to the sum of the squares of particle diameters. Since $D_{(3,2)}$ represents mean diameter being surface area-weighted, it is more directly related to dissolution rate because dissolution is a surface phenomenon. Sauter's mean diameter is more sensitive to changes in the fine particle fraction, which is critical for dissolution. Sauter's mean diameter of the sample can be measured using a Malvern particle size analyzer.

As used herein, the term "volume-weighted mean diameter" or "De Brouckere mean diameter" or "$D_{(4,3)}$" refers to the average particle size weighted by volume. It emphasizes larger particles in a distribution.

As used herein "$D_{10}$" or "D (10)" refers to the particle diameter at which 10% of the cumulative volume (or mass) of the particles in a sample are smaller than or equal to this value, as determined by a suitable particle size analysis method, such as laser diffraction. In other words, 10% of the total particle population (by volume or weight) has a diameter less than or equal to the $D_{10}$ value. For example, if a particle population has a $D_{10}$ of about 15 microns, 10% of the particles in volume or mass have a diameter of less than or equal to about 15 microns.

As used herein "$D_{50}$" or "D(50)" refers to the particle diameter at which 50% of the cumulative volume (or mass) of the particles in a sample are smaller than or equal to this value, as determined by a suitable particle size analysis method, such as laser diffraction. In other words, 50% of the total particle population (by volume or weight) has a diameter less than or equal to the $D_{50}$ value. For example, if a particle population has a $D_{50}$ of about 55 microns, 50% of the particles in volume or mass have a diameter of less than or equal to about 55 microns.

As used herein "$D_{90}$" or "D(90)" refers to the particle diameter at which 90% of the cumulative volume (or mass) of the particles in a sample are smaller than or equal to this value, as determined by a suitable particle size analysis method, such as laser diffraction. In other words, 90% of the total particle population (by volume or weight) has a diameter less than or equal to the $D_{90}$ value. For example, if a particle population has a $D_{90}$ of about 150 microns, 90% of the particles in volume or mass have a diameter of less than or equal to about 150 microns.

As used herein, the term "specific surface area" refers to the total surface area of a particulate material per unit mass, typically expressed in units of square meters per gram ($m^2$/g) or square meters per kilogram ($m^2$/kg). The specific surface area can be measured by using a Malvern particle size analyzer.

As used herein, the term "stable" or "stability" or "stabilized" refers to physical and chemical stability of composition upon storage for a specific time and condition. In one embodiment of the invention, stability after storage for at least 12 months at a temperature of 25° C. refers to the long-term stability of the solid oral composition of chlorthalidone. In another embodiment, stability after storage for at least 24 months at a temperature of 25° C. also refers to the long-term stability of the solid oral composition of chlorthalidone. In another embodiment, stability after storage for at least 36 months at a temperature of 25° C. also refers to the long-term stability of the solid oral composition of chlorthalidone. It is to be understood that, throughout the specification disclosed, the storage condition of 25° C. means 25° C.±2° C. and relative humidity of 60%±5% RH, which is as per the international regulatory guidelines representing room temperature storage of drug product in a pharmacy/hospital shelf. In further embodiment, the stability of the composition is measured by evaluating physical and chemical quality parameters like, disintegration time, impurities such as % w/w of impurity –B, % w/w of chlorthalidone ethyl ether impurity, and % w/w of total impurities.

As used herein, the term "accelerated stability" refers to physical and chemical stability of composition upon storage for a specific time and condition. In one embodiment of the invention, stability after storage for 6 months at a temperature of 40° C. and 75% relative humidity refers to the acceleration stability of the solid oral composition of chlorthalidone. It is to be understood that, throughout the specification disclosed, the storage condition of 40° C. means 40° C.±2° C. and relative humidity of 75%±5% RH. In further embodiment, the stability of the composition is measured by evaluating physical and chemical quality parameters like disintegration time, impurities such as % w/w of impurity-B, % w/w of chlorthalidone ethyl ether impurity, % w/w of total impurities.

As used herein, the term "relative humidity (RH)" refers in the context of pharmaceutical stability testing, defined as the percentage of moisture in the air relative to the maximum amount the air can hold at a given temperature. It is a key environmental parameter used in stability studies to assess how a drug product responds to different humidity conditions over time. Controlled RH levels (e.g., 60% RH at 25° C. for long-term, 75% RH at 40° C. for accelerated testing) are used during storage to simulate storage conditions and evaluate the product's physical, chemical, and microbiological stability, ensuring it remains safe and effective throughout its shelf life.

As used herein, the term "total impurities" refers to summation of all known, unknown and degradation impurities of oral tablet composition of chlorthalidone measured using HPLC.

As used herein, the term "rapidly disintegrating" refers to the time required by the tablet to disintegrate in given dissolution media. In some embodiments, rapidly disintegrating tablet disintegrates in less than 60 seconds. In other embodiments, a rapidly disintegrating tablet disintegrates in less than 50 seconds. In certain embodiments, rapidly disintegrating tablet disintegrates in less than 40 seconds. In further embodiments, rapidly disintegrating tablet disintegrates in less than 30 seconds.

As used herein, the term "subject" refers to a human or non-human animal, preferably a mammal, that is in need of or undergoing medical intervention, including therapeutic, palliative, or prophylactic treatment. In certain embodiments, the subject is a human patient suffering from, diagnosed with, or at risk of developing a condition, disease, or disorder addressed by the method described herein.

In some embodiments, the present invention provides a solid oral composition comprising chlorthalidone and a pharmaceutically acceptable excipient. In other embodiments, the present invention provides a solid oral composition comprising chlorthalidone and pharmaceutically acceptable excipient selected from group consisting of a diluent, a disintegrant, a glidant, a lubricant or a mixture thereof.

Formulating chlorthalidone composition is challenging due to its poor solubility, low permeability, particle variability, and stability concerns. In a present invention applicant has tried to address the issue through holistic approach using techniques such as controlled particle engineering. Solubility generally refers to the maximum amount of a drug that can dissolve in a given solvent under specific conditions, forming a homogeneous solution. Both solubility and the process of dissolution are governed by surface phenomena. When a solid drug particle comes into contact with a solvent (usually gastrointestinal fluids in oral delivery), dissolution begins at the surface of the drug particle which is in contact with liquid. The solvent molecules surround and interact with the outermost drug molecules, breaking intermolecular bonds and allowing those molecules to enter the solution. Therefore, for the poorly water-soluble drugs such as chlorthalidone, the more points of contact exist between the drug and the solvent when the particles are smaller in size which results into the faster dissolution.

However, overly fine drug particles, while potentially improving dissolution, can lead to several formulation and manufacturing challenges. Their high surface area and cohesive nature result in poor flowability, making processing and uniform mixing difficult. This can compromise content uniformity, especially in low-dose formulations. Fine particles are also prone to static charge build-up, causing handling issues and safety concerns. Additionally, they may agglomerate during manufacturing process, which reduces the effective surface area and slows dissolution. Their poor compressibility can lead to tablets with inconsistent hardness and disintegration.

In short, achieving optimum particle characteristics is essential in drug formulation, as both overly fine particles and non-uniform particle distributions present significant drawbacks. While very fine particles may enhance dissolution, they can cause processing issues such as poor flow, agglomeration, and content uniformity problems. On the other hand, larger or unevenly distributed particles may lead to inconsistent drug release and reduced bioavailability.

Chlorthalidone is BCS Class IV drug, which presents significant challenges in achieving consistent and efficient dissolution from oral solid dosage forms. Conventional particle size descriptors such as $D_{10}$, $D_{50}$, $D_{90}$, and $D_{(4,3)}$ are often used to describe particle size distribution; however, these parameters do not directly correlate with the surface area available for dissolution, especially in formulations containing polydisperse particles. In contrast, Sauter's mean diameter which represents the diameter of a sphere with the same volume-to-surface area ratio as that of the actual particles provides a more relevant and sensitive measure in the context of dissolution rate, which is inherently surface area dependent. By optimizing and controlling Sauter's mean diameter in the formulation of chlorthalidone oral tablets, it is possible to significantly enhance the effective surface area exposed to the dissolution medium, thereby improving the dissolution profile of the drug. This approach enables the development of a more robust and reliable oral dosage form of chlorthalidone with desired dissolution performance. Therefore, to address the above challenges, the present invention provides a solid oral composition comprising chlorthalidone having an optimum range of Sauter's mean diameter ($D_{3,2}$), which significantly improve solubility and dissolution for BCS class IV drugs.

In some embodiments, the present invention provides a solid oral composition comprising: chlorthalidone, or a pharmaceutically acceptable salt thereof, having a Sauter's mean diameter ($D_{3,2}$) of from about 8 μm to about 14 μm; and a pharmaceutically acceptable carrier comprising an excipient selected from: a diluent; a disintegrant; a glidant; a lubricant; and a combination of two or more thereof.

In certain embodiments, the present invention provides a solid oral composition comprising chlorthalidone as a pharmaceutically active ingredient having the Sauter's mean diameter ($D_{3,2}$) from about 7 μm to about 15 μm, and pharmaceutically acceptable excipient selected from group consisting of a diluent, a disintegrant, a glidant, a lubricant or a mixture thereof. In further embodiments, the present invention provides the composition having the Sauter's mean diameter ($D_{3,2}$) from about 8 μm to about 14 μm. In other embodiments, the present invention provides the composition having the Sauter's mean diameter ($D_{3,2}$) from about 9 μm to about 13 μm.

In some embodiments, the present invention provides a solid oral composition comprising chlorthalidone as a pharmaceutically active ingredient having the specific surface area of from about 0.2 m²/g to about 1 m²/g, and a pharmaceutically acceptable excipient selected from group consisting of a diluent, a disintegrant, a glidant, a lubricant or a mixture thereof. In some embodiments, the chlorthalidone, or a pharmaceutically acceptable salt thereof, has a specific surface area from about 0.25 m²/g to about 1 m²/g, about 0.25 m²/g to about 0.95 m²/g, about 0.25 m²/g to about 0.9 m²/g, about 0.25 m²/g to about 0.85 m²/g, about 0.25 m²/g to about 0.8 m²/g, about 0.25 m²/g to about 0.75 m²/g, about 0.25 m²/g to about 0.7 m²/g, about 0.25 m²/g to about 0.65 m²/g, about 0.25 m²/g to about 0.6 m²/g, about 0.25 m²/g to about 0.55 m²/g, or about 0.25 m²/g to about 0.5 m²/g. In some embodiments, the present invention provides chlorthalidone, or a pharmaceutically acceptable salt thereof, having a specific surface area of at least about 0.2 m²/g, at least about 0.25 m²/g, at least about 0.3 m²/g, at least about 0.35 m²/g, at least about 0.4 m²/g, at least about 0.45 m²/g, at least about 0.5 m²/g, at least about 0.55 m²/g, at least about 0.6 m²/g, at least about 0.65 m²/g, at least about 0.7 m²/g, at least about 0.75 m²/g, at least about 0.8 m²/g, at least about 0.85 m²/g, at least about 0.9 m²/g, at least about 0.95 m²/g or at least about 1 m²/g.

In some embodiments, the present invention provides a solid oral composition comprising: chlorthalidone, or a pharmaceutically acceptable salt thereof, having: (a) a Sauter's mean diameter ($D_{3,2}$) from about 8 μm to about 14 μm; and (b) a specific surface area from about 0.25 m²/g to about 1 m²/g; and a pharmaceutically acceptable carrier comprising an excipient selected from: a diluent; a disintegrant; a glidant; a lubricant; and a combination of two or more thereof.

In other embodiments, the present invention provides a composition comprising chlorthalidone as the active pharmaceutical ingredient, wherein the composition is formulated as a solid oral dosage form, such as a tablet, designed to provide rapid and consistent dissolution. In further embodiments, the present invention provides an oral composition comprising chlorthalidone which exhibits a dissolution profile that releases not less than about 58% of the chlorthalidone within 15 minutes in dissolution media having a pH of 1.2, 4.5, or 6.8; and wherein the dissolution testing is conducted in a USP Type I (basket) apparatus at 100 rpm in 500 ml of dissolution media maintained at 37±0.5° C.

In certain embodiments, the present invention provides a solid oral composition comprising: chlorthalidone, or a pharmaceutically acceptable salt thereof, having a Sauter's mean diameter ($D_{3,2}$) of from about 8 μm to about 14 μm; and a pharmaceutically acceptable carrier comprising an excipient selected from: a diluent; a disintegrant; a glidant; a lubricant; and a combination of two or more thereof; wherein the composition releases not less than about 58% of the chlorthalidone within 15 minutes in dissolution media having a pH of 1.2, 4.5, or 6.8; and wherein the dissolution testing is conducted in a USP Type I (basket) apparatus at 100 rpm in 500 ml of dissolution media maintained at 37±0.5° C.

In other embodiments, the present invention provides a solid oral composition comprising: chlorthalidone, or a pharmaceutically acceptable salt thereof, having: (a) a Sauter's mean diameter ($D_{3,2}$) from about 8 μm to about 14 μm; and (b) a specific surface area from about 0.25 m²/g to about 1 m²/g; and a pharmaceutically acceptable carrier comprising an excipient selected from: a diluent; a disintegrant; a glidant; a lubricant; and a combination of two or more thereof; wherein the composition releases not less than about 58% of the chlorthalidone within 15 minutes in dissolution media having a pH of 1.2, 4.5, or 6.8; and wherein the dissolution testing is conducted in a USP Type I (basket) apparatus at 100 rpm in 500 ml of dissolution media maintained at 37±0.5° C.

In further embodiments, the present invention provides a solid oral composition comprising chlorthalidone, wherein the composition releases not less than about 80% of chlorthalidone within 30 minutes in dissolution media having a pH of 1.2, pH 4.5, or pH 6.8; and wherein the dissolution testing is conducted in a USP Type I (basket) apparatus at 100 rpm in 500 ml of dissolution media maintained at 37±0.5° C. In other embodiments, the present invention provides a solid oral composition comprising chlorthalidone, wherein the composition releases not less than about 84% of chlorthalidone within 45 minutes in dissolution media having a pH of 1.2, pH 4.5, or pH 6.8; and wherein the dissolution testing is conducted in a USP Type I (basket) apparatus at 100 rpm in 500 ml of dissolution media maintained at 37±0.5° C. Still further embodiments of the present invention provide a solid oral composition comprising chlorthalidone, wherein the composition releases not less than about 90% of chlorthalidone within 60 minutes in dissolution media having a pH of 1.2, pH 4.5, or pH 6.8; and wherein the dissolution testing is conducted in a USP Type I (basket) apparatus at 100 rpm in 500 ml of dissolution media maintained at 37±0.5° C.

Yet other embodiments of the present invention provide a solid oral composition comprising: chlorthalidone, or a pharmaceutically acceptable salt thereof, having a Sauter's mean diameter ($D_{3,2}$) of from about 8 μm to about 14 μm; and a pharmaceutically acceptable carrier comprising an excipient selected from: a diluent; a disintegrant; a glidant; a lubricant; and a combination of two or more thereof; wherein the oral composition having chlorthalidone or pharmaceutically acceptable slats thereof comprises at least one of (a) to (c): (a) the release of not less than about 58% of chlorthalidone within 15 minutes in 500 ml 0.1 N hydrochloric acid as the dissolution media having a pH of about 1.2; (b) the release of not less than about 58% of chlorthalidone within 15 minutes in 500 ml acetate buffer as the dissolution media having a pH of about 4.5, and (c) the release of not less than about 58% of chlorthalidone within 15 minutes in 500 ml phosphate buffer as the dissolution media having a pH of about 6.8, wherein the dissolution testing is conducted in a USP Type I basket apparatus at 100 rpm in dissolution media maintained at 37±0.5° C. In some embodiments, the present invention provides a solid oral composition comprising chlorthalidone, or pharmaceutically acceptable salt thereof, comprising at least two of (a) to (c). In some embodiments, the present invention provides a solid oral composition comprising chlorthalidone, or pharmaceutically acceptable salt thereof, comprising (a) to (c).

In certain embodiments, the present invention provides a solid oral composition comprising chlorthalidone, wherein the dissolution testing of the composition is conducted in a USP Type I (basket) apparatus at 100 rpm in 500 ml of 0.1N hydrochloric acid having pH of 1.2 maintained at 37±0.5° C. In further embodiments, the dissolution media at pH 1.2 comprises 500 ml of 0.1 N hydrochloric acid solution. Still further embodiments of the present invention provide a solid oral composition comprising chlorthalidone, wherein the composition releases not less than about 58%, not less than about 59%, not less than about 60%, not less than about 61%, not less than about 62%, not less than about 63%, not less than about 64%, not less than about 65%, not less than about 66%, not less than about 67%, not less than about 68%, or not less than about 69% of chlorthalidone within 15 minutes in dissolution media at pH 1.2, wherein the dissolution testing is conducted in a USP Type I (basket) apparatus at 100 rpm in 500 ml of 0.1 N hydrochloric acid dissolution media maintained at 37±0.5° C. In some embodiments, the present invention provides a solid oral composition comprising chlorthalidone, wherein the composition releases not less than about 80%, not less than about 81%, not less than about 82%, not less than about 83%, not less than about 84%, not less than about 85%, not less than about 86%, not less than about 87%, not less than about 88%, not less than about 89%, not less than about 90%, or not less than about 91% of chlorthalidone within 30 minutes in dissolution media at pH 1.2, wherein the dissolution testing is conducted in a USP Type I (basket) apparatus at 100 rpm in 500 ml of 0.1 N hydrochloric acid dissolution media maintained at 37±0.5° C. Yet other embodiments of the present invention provide a solid oral composition comprising chlorthalidone, wherein the composition releases not less than about 84%, not less than about 85%, not less than about 86%, not less than about 87%, not less than about 88%, not less than about 89%, not less than about 90%, not less than about 91%, not less than about 92%, not less than about 93%, not less than about 94%, or not less than about 95% of chlorthalidone within 45 minutes in dissolution media at pH 1.2, wherein the dissolution testing is conducted in a USP Type I (basket) apparatus at 100 rpm in 500 ml of 0.1 N hydrochloric acid dissolution media maintained at 37±0.5° C. In other embodiments, the present invention provides a solid oral composition comprising chlorthalidone, wherein the composition releases not less than about 90%, not less than about 95%, not less than about 96%, not less than about 97%, not less than about 98%, or not less than about 99% of chlorthalidone within 60 minutes in dissolution media at pH 1.2, wherein the dissolution testing is conducted in a USP Type I (basket) apparatus at 100 rpm in 500 ml of 0.1 N hydrochloric acid dissolution media maintained at 37±0.5° C.

In certain embodiments, the present invention provides a solid oral composition comprising chlorthalidone, wherein the dissolution testing of the composition is conducted in a USP Type I (basket) apparatus at 100 rpm in 500 ml of acetate buffer having pH of 4.5 maintained at 37±0.5° C. In further embodiments, the dissolution media at pH 4.5 comprises 500 ml of acetate buffer solution. In other embodiments, the present invention provides the solid oral composition comprising chlorthalidone, wherein the composition releases not less than about 58%, not less than about 59%, not less than about 60%, not less than about 61%, or not less than about 62% of chlorthalidone within 15 minutes in dissolution media at pH 4.5, wherein the dissolution testing is conducted in a USP Type I (basket) apparatus at 100 rpm in 500 ml of acetate buffer dissolution media maintained at 37±0.5° C. In some embodiments, the present invention provides a solid oral composition comprising chlorthalidone, wherein the composition releases not less than about 80%, not less than about 81%, or not less than about 82% of chlorthalidone within 30 minutes in dissolution media at pH 4.5, wherein the dissolution testing is conducted in a USP Type I (basket) apparatus at 100 rpm in 500 ml of acetate buffer dissolution media maintained at 37±0.5° C. In other embodiments, the present invention provides a solid oral composition comprising chlorthalidone, wherein the composition releases not less than about 84%, not less than about 85%, not less than about 86%, not less than about 87%, not less than about 88%, or not less than about 89% of chlorthalidone within 45 minutes in dissolution media at pH 4.5, wherein the dissolution testing is conducted in a USP Type I (basket) apparatus at 100 rpm in 500 ml of acetate buffer dissolution media maintained at 37±0.5° C. In further embodiments, the present invention provides a solid oral composition comprising chlorthalidone, wherein the composition releases not less than about 90%, not less than about 91%, or not less than about 92% of chlorthalidone within 60 minutes in dissolution media at pH 4.5, wherein the dissolution testing is conducted in a USP Type I (basket) apparatus at 100 rpm in 500 ml of acetate buffer dissolution media maintained at 37±0.5° C.

In some embodiments, the present invention provides a solid oral composition comprising chlorthalidone, wherein the dissolution testing of the composition is conducted in a USP Type I (basket) apparatus at 100 rpm in 500 ml of phosphate buffer having pH of 6.8 maintained at 37±0.5° C. In further embodiments, the dissolution media at pH 6.8 comprises 500 ml of phosphate buffer solution. In other embodiments, the present invention provides a solid oral composition comprising chlorthalidone, wherein the composition releases not less than about 58%, not less than about 59%, not less than about 60%, not less than about 61%, not less than about 62%, not less than about 63%, not less than about 64%, not less than about 65%, not less than about 66%, not less than about 67%, or not less than about 68% of chlorthalidone within 15 minutes in dissolution media at pH 6.8, wherein the dissolution testing is conducted in a USP Type I (basket) apparatus at 100 rpm in 500 ml of phosphate buffer dissolution media maintained at 37±0.5° C. In certain embodiments, the present invention provides a solid oral composition comprising chlorthalidone, wherein the composition releases not less than about 80%, not less than about 81%, not less than about 82%, not less than about 83%, or not less than about 84% of chlorthalidone within 30 minutes in dissolution media at pH 6.8, wherein the dissolution testing is conducted in a USP Type I (basket) apparatus at 100 rpm in 500 ml of phosphate buffer dissolution media maintained at 37±0.5° C. In some embodiments, the present invention provides a solid oral composition comprising chlorthalidone, wherein the composition releases not less than about 84%, not less than about 85%, not less than about 86%, not less than about 87%, not less than about 88%, not less than about 89%, not less than about 90%, or not less than about 91% of chlorthalidone within 45 minutes in dissolution media at pH 6.8, wherein the dissolution testing is conducted in a USP Type I (basket) apparatus at 100 rpm in 500 ml of phosphate buffer dissolution media maintained at 37±0.5° C. In further embodiments, the present invention provides a solid oral composition comprising chlorthalidone, wherein the composition releases not less than about 90%, not less than about 91%, not less than about 92%, or not less than about 93% of chlorthalidone within 60 minutes in dissolution media at pH 6.8, wherein the dissolution testing is conducted in a USP Type I (basket) apparatus at 100 rpm in 500 ml of phosphate buffer dissolution media maintained at 37±0.5° C.

In certain embodiments, the present invention provides a composition prepared with milled chlorthalidone that has enhanced dissolution when compared to a composition prepared without milled chlorthalidone. In some embodiments, the present invention provides a solid oral composition comprising: chlorthalidone, or a pharmaceutically acceptable salt thereof, having a Sauter's mean diameter $(D_{3,2})$ of from about 8 μm to about 14 μm; and a pharmaceutically acceptable carrier comprising an excipient selected from: a diluent; a disintegrant; a glidant; a lubricant; and a combination of two or more thereof; wherein the composition comprising milled chlorthalidone with the Sauter's mean diameter from about 8 μm to about 14 μm releases at least about 30% more chlorthalidone than the composition prepared without milling chlorthalidone, within 15 minutes from the start of the dissolution testing, when tested in USP Type I (basket) apparatus at 100 rpm in 500 ml of dissolution media having a pH of 1.2, 4.5, or 6.8 maintained at 37±0.5° C. In other embodiments, the present invention provides the composition comprising chlorthalidone, wherein the composition comprising milled chlorthalidone with a Sauter's mean diameter from about 8 μm to about 14 μm releases at least about 25% more chlorthalidone than the composition prepared without milling chlorthalidone, within 30 minutes from the start of the dissolution testing, when tested in USP Type I (basket) apparatus at 100 rpm in 500 ml of dissolution media having a pH of 1.2, 4.5, or 6.8 maintained at 37±0.5° C.

In some embodiments, the present invention provides a composition comprising chlorthalidone, wherein the composition comprising milled chlorthalidone with the Sauter's mean diameter from about 8 μm to about 14 μm releases at least about 20% more chlorthalidone than the composition prepared without milling chlorthalidone, within 45 minutes from the start of the dissolution testing, when tested in USP Type I (basket) apparatus at 100 rpm in 500 ml of dissolution media having a pH of 1.2, 4.5, or 6.8 maintained at 37±0.5° C. Still further embodiments of the present invention provide a composition comprising chlorthalidone, wherein the composition comprises milled chlorthalidone with the Sauter's mean diameter from about 8 μm to about 14 μm releases at least about 15% more chlorthalidone than the composition prepared without milling chlorthalidone, within 60 minutes from the start of the dissolution testing, when tested in USP Type I (basket) apparatus at 100 rpm in 500 ml of dissolution media having a pH of 1.2, 4.5, or 6.8 maintained at $37\pm0.5^{\circ}$ C.

In yet other embodiments, the present invention provides the solid oral composition comprising chlorthalidone; wherein the chlorthalidone has a specific surface area from about 0.25 $m^2/g$ to about 1 $m^2/g$.

In certain embodiments, the present invention provides chlorthalidone particles have a D90 equal to or less than about 200 micron, equal to or less than about 195 micron, equal to or less than about 190 micron, equal to or less than about 185 micron, equal to or less than about 180 microns, equal to or less than about 175 micron, equal to or less than about 170 micron, equal to or less than about 165 micron, equal to or less than about 160 s, equal to or less than about 155 microns, equal to or less than about 150 micron, equal to or less than about 145 micron, equal to or less than about 140 micron, equal to or less than about 135 micron, equal to or less than about 130 micron, equal to or less than about 125 micron, equal to or less than about 120 micron, equal to or less than about 115 micron, or equal to or less than about 110 micron.

In other embodiments, the present invention provides chlorthalidone particles having a D50 equal to or less than about 50 micron, equal to or less than about 45 micron, equal to or less than about 40 micron, equal to or less than about 36 micron, equal to or less than about 30 micron, equal to or less than about 25 micron, equal to or less than about 23 micron, equal to or less than about 22 micron, equal to or less than about 20 micron, or equal to or less than about 15 micron.

Yet other embodiments of the present invention provide chlorthalidone particles having a D10 equal to or less than about 8 microns, equal to or less than about 7 microns, equal to or less than about 6 microns, equal to or less than about 5 microns, equal to or less than about 4 microns, or equal to or less than about 3 microns.

In some embodiments, the present invention provides a solid oral composition comprising chlorthalidone, wherein the composition is in a form selected from: a tablet; a capsule; a pellet; a powder for oral suspension; granules; and lozenges. In one embodiment, the present invention provides the solid oral composition comprising chlorthalidone in a tablet form. In other embodiments, the tablet form of the pharmaceutical composition comprising chlorthalidone is selected from immediate release tablet. Still further embodiments of the present invention provide an oral tablet comprising chlorthalidone wherein the tablet is unscored. In some embodiments, the present invention provides the oral tablet composition comprising chlorthalidone, wherein the tablet cannot be split further.

Some embodiments of the present invention provide a solid oral pharmaceutical composition comprising chlorthalidone and pharmaceutically acceptable excipients selected from: a diluent; a disintegrant; a glidant; a lubricant; and a combination of two or more thereof.

In some embodiments, the present invention provides a composition wherein the diluent is selected from a group consisting of lactose (including monohydrate, anhydrous, and spray-dried forms), microcrystalline cellulose, powdered cellulose, dicalcium phosphate (anhydrous or dihydrate), tricalcium phosphate, calcium carbonate, calcium sulfate, mannitol, sorbitol, xylitol, maltitol, isomalt, erythritol, dextrose, sucrose, fructose, trehalose, low-substituted hydroxypropyl cellulose, hydroxypropyl cellulose, hydroxypropyl methylcellulose, methylcellulose, ethyl cellulose or a mixture thereof. In one embodiment the diluent is microcrystalline cellulose.

In certain embodiments, the present invention provides a composition wherein the disintegrant is selected from a group consisting of starch-based materials such as maize starch, pregelatinized starch, and sodium starch glycolate; cellulose derivatives such as croscarmellose sodium, cross-linked sodium carboxymethyl cellulose, and low-substituted hydroxypropyl cellulose; as well as synthetic super disintegrants including crospovidone (cross-linked polyvinylpyrrolidone), alginic acid, calcium alginate, and sodium alginate, as well as natural gums such as guar gum and xanthan gum or a mixture thereof. In one embodiment, the disintegrant is selected from pregelatinized starch and sodium starch glycolate, or mixture thereof.

In some embodiments, the present invention provides a composition wherein the glidant is selected from a group consisting of colloidal silicon dioxide, talc, magnesium trisilicate, starch, and calcium silicate, syloid (amorphous silica), tribasic calcium phosphate or a mixture thereof. In some embodiments, the glidant is selected from colloidal silicon dioxide.

In some embodiments, the present invention provides a composition wherein the lubricant is selected from a group consisting of magnesium stearate, calcium stearate, stearic acid, sodium stearyl fumarate, hydrogenated vegetable oils, glyceryl behenate, and polyethylene glycol (PEG) of various molecular weights, particularly PEG 4000 and PEG 6000, zinc stearate, talc, mineral oil or a mixture thereof. In further embodiments, the lubricant requires a calcium stearate.

In certain embodiments, the present invention provides an oral tablet comprising chlorthalidone which rapidly disintegrates in dissolution media. In further embodiments, the present invention provides an oral care tablet comprising: chlorthalidone, or a pharmaceutically acceptable salt thereof, having a Sauter's mean diameter ($D_{3,2}$) of from about 8 $\mu$m to about 14 $\mu$m; and a pharmaceutically acceptable carrier comprising an excipient selected from: a diluent; a disintegrant; a glidant; a lubricant; and a combination of two or more thereof; wherein the composition releases not less than about 58% of the chlorthalidone within 15 minutes in dissolution media having a pH of 1.2, 4.5, or 6.8; and wherein the dissolution testing is conducted in a USP Type I (basket) apparatus at 100 rpm in 500 ml of dissolution media maintained at $37\pm0.5^{\circ}$ C.; and wherein the tablet substantially disintegrates in the dissolution media in less than about 60 seconds.

In further embodiments, the invention provides the tablet substantially disintegrates in the dissolution media selected from in less than about 50 seconds, in less than about 45 seconds, in less than about 40 seconds, in less than about 35 seconds, in less than about 30 seconds, or in less than about 25 seconds.

In some embodiments, the present invention provides the tablet composition of chlorthalidone as an active ingredient and a pharmaceutically acceptable excipient selected from group consisting of a diluent, a disintegrant, a glidant, a lubricant or a mixture thereof, wherein the tablet comprises about 12.5 mg of chlorthalidone, or a pharmaceutically acceptable salt thereof.

In various embodiments, the present invention provides a composition having desired particle characteristics such that along with desired dissolution profile, the composition also has excellent storage stability. It is of utmost importance to take care that reducing the particle size yields the fine particle with higher solubility but lacks the long-term stability of the composition as excessive increase in surface area may increase the probability of higher impurity generation. Therefore, it is challenging to have chlorthalidone as an active ingredient with the desired particle characteristics with specific Sauter's mean diameter and specific surface area along with a robust long-term stability of the composition. The present invention has carefully balanced the particle characteristics, so that it can give desired dissolution profile of the poorly soluble drug at the same time does not compromise the long term stability of the composition with improved powder handling and reduced static electricity risk.

In some embodiments, the present invention provides a composition comprising chlorthalidone with a desired particle characteristic with specific Sauter's mean diameter and specific surface area, which is chemically and physically stable, wherein the composition remains stable after storage at long term stability condition or accelerated storage condition. The long-term storage condition for the composition is selected as 25° C. and 60% RH for at least about 12 months or 24 months or 36 months, whereas the accelerated storage condition is selected as 40° C. at 75% RH for 6 months.

In further embodiments, the present invention provides a solid oral composition comprising chlorthalidone as a pharmaceutically active ingredient having the Sauter's mean diameter ($D_{3,2}$) from about 8 μm to about 14 μm; and a pharmaceutically acceptable excipient selected from a diluent; a disintegrant; a glidant; a lubricant; and a combination of two or more thereof; wherein the composition after storage at 25° C. and 60% relative humidity for at least 12 months, or after storage at 40° C. and 75% relative humidity for 6 months has at least two of (a) to (c): (a) the total impurities in an amount that does not exceed about 1%; (b) impurity B in an amount that does not exceed about 0.5%; and (c) chlorthalidone ethyl ether impurity in an amount that does not exceed about 0.1%; wherein the impurity concentrations are calculated based on the weight of chlorthalidone. In some embodiments, the present invention provides a solid oral composition, wherein the composition after storage at 25° C. and 60% relative humidity for at least 12 months, or after storage at 40° C. and 75% relative humidity for 6 months has impurity levels of (a) to (c). In certain embodiments, the present invention provides a solid oral composition, wherein the composition after storage at 40° C. and 75% relative humidity for 6 months has impurity levels of (a) to (c).

In some of the above embodiments, the present invention provides a solid oral composition, wherein the composition after storage at 25° C. and 60% relative humidity for at least 24 months, optionally at least 36 months, has at least two of (a) to (c):

(a) the total impurities in an amount that does not exceed about 1%;

(b) impurity B in an amount that does not exceed about 0.5%;

(c) chlorthalidone ethyl ether impurity in an amount that does not exceed about 0.1%;

wherein the impurity concentrations are calculated based on the weight of chlorthalidone. In some embodiments, the composition after storage at 25° C. and 60% relative humidity for at least 24 months or at least 36 months has impurity levels of (a) to (c).

In some embodiments, the present invention provides a solid oral composition comprising:

(i) chlorthalidone, or a pharmaceutically acceptable salt thereof, having a Sauter's mean diameter ($D_{3,2}$) of from about 8 μm to about 14 μm; and (ii) a pharmaceutically acceptable carrier comprising an excipient selected from: a diluent; a disintegrant; a glidant; a lubricant; and a combination of two or more thereof;

wherein the composition releases not less than about 58% of the chlorthalidone within 15 minutes in dissolution media having a pH of 1.2, 4.5, or 6.8; and wherein the dissolution testing is conducted in a USP Type I (basket) apparatus at 100 rpm in 500 ml of dissolution media maintained at 37±0.5° C.;

wherein the composition after storage at 25° C. and 60% relative humidity for at least 12 months, or after storage at 40° C. and 75% relative humidity for 6 months has at least two of (a) to (c):

(a) the total impurities in an amount that does not exceed about 1%;

(b) impurity B in an amount that does not exceed about 0.5%;

(c) chlorthalidone ethyl ether impurity in an amount that does not exceed about 0.1%;

wherein the impurity concentrations are calculated based on the weight of chlorthalidone.

In various embodiments, the present invention provides the composition, wherein the total impurities in the composition are not more than 1% w/w, after storage for at least about 12 months or at least about 24 months or at least about 36 months at a temperature of 25° C. and 60% RH when analyzed by HPLC. In other embodiments, the present invention provides a chlorthalidone containing composition, wherein the total impurities in the composition are selected from the group consisting of not more than 1% w/w, not more than 0.9% w/w, or not more than 0.8% w/w after storage for 12 months or 24 months or 36 months at a temperature of 25° C. and 60% RH when analyzed by HPLC.

In some embodiments, the present invention provides a solid oral composition comprising chlorthalidone, or a pharmaceutically acceptable salt thereof, wherein the impurity-B in the composition is not more than 0.5% w/w, after storage for at least about 12 months or at least about 24 months or at least about 36 months at a temperature of 25° C. and 60% RH when analyzed by HPLC. In further embodiments, the present invention provides a solid oral composition comprising chlorthalidone, or a pharmaceutically acceptable salt thereof, wherein the total impurities in the composition are selected from the group consisting of not more than 0.5% w/w, or not more than 0.4% after storage for at least about 12 months or at least about 24 months or at least about 36 months at a temperature of 25° C. and 60% RH when analyzed by HPLC.

In certain embodiments, the present invention provides a solid oral composition comprising chlorthalidone, or a pharmaceutically acceptable salt thereof, wherein the chlorthalidone ethyl ether impurity in the composition does not exceed 0.1% w/w, after storage for at least about 12 months or at least about 24 months or at least about 36 months at a temperature of 25° C. and 60% RH when analyzed by HPLC. In other embodiments, the present invention provides a solid oral composition comprising chlorthalidone, or a pharmaceutically acceptable salt thereof, wherein the chlorthalidone ethyl ether impurity in the composition does not exceed the value selected from the group consisting of 0.1% w/w, 0.09% w/w, or 0.08% w/w after storage for at least about 12 months or at least about 24 months or at least about 36 months at a temperature of 25° C. and 60% RH when analyzed by HPLC.

In yet other embodiments, the present invention provides a solid oral composition comprising chlorthalidone, or a pharmaceutically acceptable salt thereof, wherein the total impurities in the composition are not more than 1% w/w, after storage for 6 months at a temperature of 40° C. and 75% RH when analyzed by HPLC. In some embodiments, the present invention provides a solid oral composition comprising chlorthalidone, or a pharmaceutically acceptable salt thereof, wherein the total impurities in the composition are not more than 1% w/w, not more than 0.9% w/w, or not more than 0.8% w/w after storage for 6 months at a temperature of 40° C. and 75% RH when analyzed by HPLC.

In various embodiments, the present invention provides a solid oral composition comprising chlorthalidone, or a pharmaceutically acceptable salt thereof, wherein the impurity-B in the composition is not more than 0.5% w/w, after storage for 6 months at a temperature of 40° C. and 75% RH when analyzed by HPLC. In certain embodiments, the present invention provides a solid oral composition comprising chlorthalidone, or a pharmaceutically acceptable salt thereof, wherein the total impurities in the composition are not more than 0.5% w/w, or not more than 0.4% after storage for 6 months at a temperature of 40° C. and 75% RH when analyzed by HPLC.

In certain embodiments, the present invention provides a solid oral composition comprising chlorthalidone, or a pharmaceutically acceptable salt thereof, wherein the chlorthalidone ethyl ether impurity in the composition does not exceed 0.1% w/w, after storage for 6 months at a temperature of 40° C. and 75% RH when analyzed by HPLC. In other embodiments, the present invention provides a solid oral composition comprising chlorthalidone, or a pharmaceutically acceptable salt thereof, wherein the chlorthalidone ethyl ether impurity in the composition does not exceed 0.1% w/w, 0.09% w/w, or 0.08% w/w after storage for 6 months at a temperature of 40° C. and 75% RH when analyzed by HPLC.

The present invention also provides a solid oral composition comprising chlorthalidone which is prepared by the process comprising steps such as milling, sifting, blending, mixing, and direct compression. The milling process becomes crucial for an oral tablet composition containing chlorthalidone which has poorly aqueous solubility and permeability as well as has erratic absorption window thereby imparting varying bioavailability. Even modest improvements in dissolution can significantly impact the extent and rate of absorption, and consequently, the bioavailability.

In the pharmaceutical industry, particle size reduction is a critical step in improving the solubility, dissolution rate, and bioavailability of drug substances. The milling process is used to reduce the particle size of the drug substance, thereby increasing the surface area available for dissolution which can lead to an improved dissolution and uniform absorption of drug into GIT. Various milling techniques are employed for this purpose, including jet milling, ball milling, hammer milling, and fluid energy milling, each selected based on the physicochemical properties of the drug and desired particle size distribution. Among these, the Fitz mill also known as a comminuting mill, holds particular importance due to its versatility and efficiency in producing uniform particle sizes suitable for downstream processing such as granulation and tableting. The Fitz mill operates on the principle of impact and attrition, wherein the material is fed into a chamber containing a rotating rotor with fixed or replaceable blades that force the material against a screen or sieve. This action causes the particles to break down through mechanical stress, allowing only suitably sized particles to pass through the screen. Its ability to control particle size distribution precisely by changing screen types and impeller speeds makes the Fitz mill especially valuable in the development and scale-up of oral solid dosage forms.

In such a composition, achieving a uniform and sufficiently small particle size distribution through controlled milling can improve not only the dissolution kinetics but also the content uniformity of the dosage form. Moreover, milling can improve the blend uniformity and compressibility of the formulation by ensuring a consistent particle size range across excipients and actives, which is crucial for direct compression processes. However, a balanced approach to milling is necessary, as excessive milling may result in undesirable effects such as amorphization, thermal degradation, or static charge buildup, all of which could compromise the stability and manufacturability of the drug product.

In some embodiments, the present invention provides a solid oral composition comprising chlorthalidone; a pharmaceutically acceptable excipient selected from: a diluent; a disintegrant; a glidant; a lubricant; and a combination of two or more thereof, wherein the composition is prepared by a process comprises milling of chlorthalidone, wherein the milling step is selected from the group consisting of jet mill, ball mill, hammer mill, fluid energy mill or Fitz mill to achieve desired particle characteristics. In other embodiments, the milling step comprises the use of a Fitz mill.

In certain embodiments, the present invention provides a solid oral composition comprising chlorthalidone, or a pharmaceutically acceptable salt thereof; and a pharmaceutically acceptable excipient selected from: a diluent; a disintegrant; a glidant; a lubricant; and a combination of two or more thereof; wherein the composition is prepared by a process comprising milling of chlorthalidone through Fitz mill to achieve desired particle characteristics.

In other embodiments, the present invention provides a solid oral composition comprising:
- (i) chlorthalidone, or a pharmaceutically acceptable salt thereof, having a Sauter's mean diameter ($D_{3,2}$) of from about 8 μm to about 14 μm; and
- (ii) a pharmaceutically acceptable carrier comprising an excipient selected from: a diluent; a disintegrant; a glidant; a lubricant; and a combination of two or more thereof;
- wherein the composition releases not less than about 58% of the chlorthalidone within 15 minutes in dissolution media having a pH of 1.2, 4.5 or 6.8; and
- wherein the dissolution testing is conducted in a USP Type I (basket) apparatus at 100 rpm in 500 ml of dissolution media maintained at 37±0.5° C.; and
- wherein the solid oral composition is prepared by the method comprising, passing chlorthalidone through Fitz-mill using a 0.020" screen, with knives in reverse position, at a speed of about 4700 rpm at a feed rate of approximately 150 g/minute and re-milling the material under the same conditions to provide chlorthalidone having the Sauter's mean diameter ($D_{3,2}$) from about 8 μm to about 14 μm. In some of the above embodiments, the present invention provides a composition wherein the composition is prepared by a process comprising a milling step which provides chlorthalidone having a specific surface area of from about 0.25 m²/g to about 1 m²/g.

In some embodiments, the present invention provides a method of preparing the composition, wherein the speed of Fitz mill is about 4500 rpm, 4600 rpm, about 4700 rpm, about 4800 rpm, about 4900 rpm or about 5000 rpm.

In further embodiments, the present invention provides a solid oral composition comprising chlorthalidone, or a pharmaceutically acceptable salt thereof; and a pharmaceutically acceptable excipient selected from: a diluent; a disintegrant; a glidant; a lubricant; and a combination of two or more thereof; wherein the composition is prepared by a process comprising milling of chlorthalidone through Fitz mill to achieve desired particle characteristics.

In some embodiments, the present invention provides the method of preparing a solid oral composition of chlorthalidone, or a pharmaceutically acceptable salt thereof, having a Sauter's mean diameter (D$_{3,2}$) of from about 8 μm to about 14 μm; and a pharmaceutically acceptable carrier comprising an excipient selected from: a diluent; a disintegrant; a glidant; a lubricant; and a combination of two or more thereof, comprises:

(a) passing an effective amount of chlorthalidone, or a pharmaceutically acceptable salt thereof, through a Fitz Mill using a screen;

(b) re-milling the product of step (a) to provide a chlorthalidone, or a pharmaceutically acceptable salt thereof, having a Sauter's mean diameter (D$_{3,2}$) of from about 8 μm to about 14 μm;

(c) sifting sodium starch glycolate, portion of colloidal silicon dioxide, and pregelatinized starch through a sieve;

(d) premixing microcrystalline cellulose in a V-blender;

(e) blending the product of step (b) and product of step (c) with the premixed microcrystalline cellulose from step (d) in a V-blender to form a first blend;

(f) sifting the first blend obtained in step (e), through a sieve;

(g) blending the product of step (f) in a V-blender to form a second blend;

(h) sifting a portion of colloidal silicon dioxide and a portion of the second blend from step (g), through a sieve;

(i) blending the product of step (h) in a V-blender to form a third blend;

(j) sifting calcium stearate and a portion of the third blend from step (i), through a sieve;

(k) blending the product of step (j) in a V-blender to obtain a final blend; and (l) compressing the final blend into tablets.

In other embodiments, the present invention provides a process for preparing an oral tablet comprising chlorthalidone, or a pharmaceutically acceptable salt thereof, having a Sauter's mean diameter (D$_{3,2}$) from about 8 μm to about 14 μm; and a pharmaceutically acceptable excipient selected from a diluent; a disintegrant; a glidant; a lubricant and a combination of two or more thereof, the process comprising:

(a) passing chlorthalidone through Fitz-mill using a 0.020" screen, with knives in reverse position, at a high speed of approximately 4700 rpm at a feed rate of approximately 150 g/minute and re-milling the material under the same conditions to provide chlorthalidone having the Sauter's mean diameter (D3,2) from about 8 μm to about 14 μm;

(b) sifting sodium starch glycolate, portion of colloidal silicon dioxide, and pregelatinized starch through sieve #20;

(c) premixing microcrystalline cellulose in a V-blender at approximately 21 rpm for about 4 minutes;

(d) blending the milled chlorthalidone from step (a) and sifted materials from step (b) with the premixed microcrystalline cellulose from step (c) in a V-blender at 21 rpm for about 4 minutes to form a blend;

(e) sifting the blend obtained in step (d) through Sieve #30;

(f) blending the sifted blend of step (e) for about 13 minutes at 21 rpm in a V-blender;

(g) sifting of remaining portion of colloidal silicon dioxide through Sieve #20 using a suitable portion of the step (f) blend to aid in mixing and screening;

(h) blending the sifted second portion of colloidal silicon dioxide of step (g) blend in a V-blender of step (f) for about 7 minutes at 21 rpm;

(i) sifting calcium stearate through sieve #40 using a portion of the step (h) blend to aid in mixing and screening;

(j) blending the calcium stearate with the blend from step (i) in a V-blender from step (h) for about 7 minutes at 21 rpm to obtain a final mix blend;

(k) compressing the final-mix blend into tablets using direct compression tablet press; and (l) packaging the tablets into high-density polyethylene (HDPE) containers.

In some embodiments, the present invention provides a solid oral composition comprising:

(i) chlorthalidone, or a pharmaceutically acceptable salt thereof, having a Sauter's mean diameter (D$_{3,2}$) of from about 8 μm to about 14 μm; and (ii) a pharmaceutically acceptable carrier comprising an excipient selected from: a diluent; a disintegrant; a glidant; a lubricant; and a combination of two or more thereof;

wherein the composition releases not less than about 58% of chlorthalidone within 15 minutes in dissolution media having a pH of 1.2, 4.5, or 6.8; and wherein the dissolution testing is conducted in a USP Type I basket apparatus at 100 rpm in 500 ml of dissolution media maintained at 37±0.5° C., wherein a solid oral composition is prepared by a method comprising:

(a) passing an effective amount of chlorthalidone, or a pharmaceutically acceptable salt thereof, through a Fitz Mill using a screen;

(b) re-milling the product of step (a) to provide a chlorthalidone, or a pharmaceutically acceptable salt thereof, having a Sauter's mean diameter (D$_{3,2}$) of from about 8 μm to about 14 μm;

(c) sifting sodium starch glycolate, portion of colloidal silicon dioxide, and pregelatinized starch through a sieve;

(d) premixing microcrystalline cellulose in a V-blender;

(e) blending the product of step (b) and product of step (c) with the premixed microcrystalline cellulose from step (d) in a V-blender to form a first blend;

(f) sifting the first blend obtained in step (e), through a sieve;

(g) blending the product of step (f) in a V-blender to form a second blend;

(h) sifting a portion of colloidal silicon dioxide and a portion of the second blend from step (g), through a sieve;

(i) blending the product of step (h) in a V-blender to form a third blend;

(j) sifting calcium stearate and a portion of the third blend from step (i), through a sieve;

(k) blending the product of step (j) in a V-blender to obtain a final blend; and (l) compressing the final blend into tablets.

In certain embodiments, the present invention provides an oral tablet composition comprising:

(i) chlorthalidone, or a pharmaceutically acceptable salt thereof, having a Sauter's mean diameter ($D_{3,2}$) of from about 8 μm to about 14 μm; and (ii) a pharmaceutically acceptable carrier comprising an excipient selected from: a diluent; a disintegrant; a glidant; a lubricant; and a combination of two or more thereof;

wherein the composition releases not less than about 58% of the chlorthalidone within 15 minutes in dissolution media having a pH of 1.2, 4.5 or pH 6.8; and wherein the dissolution testing is conducted in a USP Type I (basket) apparatus at 100 rpm in 500 ml of dissolution media maintained at 37±0.5° C.;

wherein the oral tablet is prepared by the method comprising:

(a) passing chlorthalidone through Fitz-mill using a 0.020" screen, with knives in reverse position, at a high speed of approximately 4700 rpm at a feed rate of approximately 150 g/minute and re-milling the material under the same conditions to provide chlorthalidone having the Sauter's mean diameter ($D_{3,2}$) from about 8 μm to about 14 μm;

(b) sifting sodium starch glycolate, portion of colloidal silicon dioxide, and pregelatinized starch through sieve #20;

(c) premixing microcrystalline cellulose in a V-blender at approximately 21 rpm for about 4 minutes;

(d) blending the milled chlorthalidone from step (a) and sifted materials from step (b) with the premixed microcrystalline cellulose from step (c) in a V-blender at 21 rpm for about 4 minutes to form a blend;

(e) sifting the blend obtained in step (d) through Sieve #30;

(f) blending the sifted blend of step (e) for about 13 minutes at 21 rpm in a V-blender;

(g) sifting of remaining portion of colloidal silicon dioxide through Sieve #20 using a suitable portion of the step (f) blend to aid in mixing and screening;

(h) blending the sifted second portion of colloidal silicon dioxide of step (g) blend in a V-blender of step (f) for about 7 minutes at 21 rpm;

(i) sifting calcium stearate through sieve #40 using a portion of the step (h) blend to aid in mixing and screening;

(j) blending the calcium stearate with the blend from step (i) in a V-blender from step (h) for about 7 minutes at 21 rpm to obtain a final mix blend;

(k) compressing the final-mix blend into tablets using direct compression tablet press; and (l) packaging the tablets into high-density polyethylene (HDPE) containers.

In other embodiments, the present invention further provides a solid oral composition comprising chlorthalidone, wherein the composition is prepared by a process comprising a milling step which provides chlorthalidone having the specific surface area from about 0.25 m²/g to about 1 m²/g.

In some embodiments, the present invention provides a solid oral composition comprising:

(i) chlorthalidone, or a pharmaceutically acceptable salt thereof, having a Sauter's mean diameter ($D_{3,2}$) of from about 8 μm to about 14 μm; and (ii) a pharmaceutically acceptable carrier comprising an excipient selected from: a diluent; a disintegrant; a glidant; a lubricant; and a combination of two or more thereof;

wherein the composition releases not less than about 58% of the chlorthalidone within 15 minutes in dissolution media having a pH of 1.2, 4.5 or 6.8; and wherein the dissolution testing is conducted in a USP Type I (basket) apparatus at 100 rpm in 500 ml of dissolution media maintained at 37±0.5° C.;

wherein the solid oral composition is in the form of tablet is prepared by the method comprising:

(a) passing chlorthalidone through Fitz-mill using a 0.020" screen, with knives in reverse position, at a high speed of approximately 4700 rpm at a feed rate of approximately 150 g/minute and re-milling the material under the same conditions to provide chlorthalidone having the Sauter's mean diameter ($D_{3,2}$) from about 8 μm to about 14 μm;

(b) sifting sodium starch glycolate, portion of colloidal silicon dioxide, and pregelatinized starch through sieve #20;

(c) premixing microcrystalline cellulose in a V-blender at approximately 21 rpm for about 4 minutes;

(d) blending the milled chlorthalidone from step (a) and sifted materials from step (b) with the premixed microcrystalline cellulose from step (c) in a V-blender at 21 rpm for about 4 minutes to form a blend;

(e) sifting the blend obtained in step (d) through Sieve #30;

(f) blending the sifted blend of step (e) for about 13 minutes at 21 rpm in a V-blender;

(g) sifting of remaining portion of colloidal silicon dioxide through Sieve #20 using a suitable portion of the step (f) blend to aid in mixing and screening;

(h) blending the sifted second portion of colloidal silicon dioxide of step (g) blend in a V-blender of step (f) for about 7 minutes at 21 rpm;

(i) sifting calcium stearate through sieve #40 using a portion of the step (h) blend to aid in mixing and screening;

(j) blending the calcium stearate with the blend from step (i) in a V-blender from step (h) for about 7 minutes at 21 rpm to obtain a final mix blend;

(k) compressing the final-mix blend into tablets using direct compression tablet press; and (l) packaging the tablets into high-density polyethylene (HDPE) containers, wherein the composition after storage at 25° C. and 60% relative humidity for at least 12 months, or after storage at 40° C. and 75% relative humidity for 6 months has at least two of (a) to (c):

(a) the total impurities in an amount that does not exceed about 1%;

(b) impurity B in an amount that does not exceed about 0.5%;

(c) chlorthalidone ethyl ether impurity in an amount that does not exceed about 0.1%;

wherein the impurity concentration are calculated based on the weight of chlorthalidone.

In other embodiments, the present invention provides a solid oral composition comprising chlorthalidone, or a pharmaceutically acceptable salt thereof, wherein when the composition is stored at 25° C. and 60% relative humidity for at least 24 months, optionally for or at least 36 months, it has at least two of (a) to (c):

(a) the total impurities in an amount that does not exceed about 1%;

(b) impurity B in an amount that does not exceed about 0.5%;

(c) chlorthalidone ethyl ether impurity in an amount that does not exceed about 0.1%; wherein the impurity concentrations are calculated based on the weight of chlorthalidone.

In some embodiments, the present invention provides a solid oral composition comprising chlorthalidone wherein the composition is prepared by a process wherein the final-mix blend is stored in double polyethylene-lined containers prior to direct compression.

In other embodiments, the present invention provides a solid oral composition comprising chlorthalidone as a pharmaceutically active ingredient having specific particle characteristics wherein the drug releases from the composition at uniform rate across different pH simulating the gastrointestinal condition of a human. In further embodiments, the chlorthalidone is formulated with unique particle characteristics, which result in less variability in absorption and bioavailability when administered to a patient.

In some embodiments, the present invention provides a method of treating, reducing, preventing or ameliorating a symptom associated with hypertension in a subject in need thereof, comprising administering to said subject in need thereof, an effective amount of a solid oral composition comprising:

(i) chlorthalidone, or a pharmaceutically acceptable salt thereof, having a Sauter's mean diameter ($D_{3,2}$) of from about 8 μm to about 14 μm; and (ii) a pharmaceutically acceptable carrier comprising an excipient selected from: a diluent; a disintegrant; a glidant; a lubricant; and a combination of two or more thereof;

wherein the composition releases not less than about 58% of the chlorthalidone within 15 minutes in dissolution media having a pH of 1.2, 4.5 or 6.8; and wherein the dissolution testing is conducted in a USP Type I (basket) apparatus at 100 rpm in 500 ml of dissolution media maintained at 37±0.5° C.

In certain embodiments, the present invention provides a method of treatment comprising administering a solid oral composition of chlorthalidone which is in the form of a tablet. In some embodiments, the present invention provides a method of treatment comprising administering a solid oral composition comprising chlorthalidone, wherein the composition releases not less than about 80% of chlorthalidone within 30 minutes in dissolution media having pH of 1.2, 4.5, or 6.8; and wherein the dissolution testing is conducted in a USP Type I (basket) apparatus at 100 rpm in 500 ml of dissolution media maintained at 37±0.5° C.

In other embodiments, the method of treatment comprises administering the solid oral composition comprising chlorthalidone, wherein the composition releases not less than about 84% of chlorthalidone within 45 minutes in dissolution media having a pH 1.2, 4.5, or 6.8; and wherein the dissolution testing is conducted in a USP Type I (basket) apparatus at 100 rpm in 500 ml of dissolution media maintained at 37±0.5° C.

In further embodiments, the method of treatment comprises administering the solid oral composition comprising chlorthalidone, wherein the composition releases not less than about 90% of chlorthalidone within 60 minutes in dissolution media having a pH 1.2, 4.5, or 6.8, wherein the dissolution testing is conducted in a USP Type I (basket) apparatus at 100 rpm in 500 ml of dissolution media maintained at 37±0.5° C.

In some embodiments, the present invention provides a method of treating, reducing, preventing or ameliorating a symptom associated with hypertension in a subject in need thereof, comprising administering to said subject in need thereof, an effective amount of a solid oral tablet composition comprising:

(i) chlorthalidone, or a pharmaceutically acceptable salt thereof, having a Sauter's mean diameter ($D_{3,2}$) of from about 8 μm to about 14 μm; and (ii) a pharmaceutically acceptable carrier comprising an excipient selected from: a diluent; a disintegrant; a glidant; a lubricant; and a combination of two or more thereof;

wherein the composition releases not less than about 58% of the chlorthalidone within 15 minutes in dissolution media having a pH of 1.2, pH 4.5, or pH 6.8; and wherein the dissolution testing is conducted in a USP Type I (basket) apparatus at 100 rpm in 500 ml of dissolution media maintained at 37±0.5° C.;

wherein the tablet composition comprising chlorthalidone is prepared by the method comprising:

(a) passing chlorthalidone through Fitz-mill using a 0.020" screen, with knives in reverse position, at a high speed of approximately 4700 rpm at a feed rate of approximately 150 g/minute and re-milling the material under the same conditions to provide chlorthalidone having the Sauter's mean diameter ($D_{3,2}$) from about 8 μm to about 14 μm;

(b) sifting sodium starch glycolate, portion of colloidal silicon dioxide, and Pregelatinized Starch through Sieve #20;

(c) premixing microcrystalline cellulose in a V-blender at approximately 21 rpm for about 4 minutes;

(d) blending the milled chlorthalidone from step (a) and sifted materials from step (b) with the premixed microcrystalline cellulose from step (c) in a V-blender at 21 rpm for about 4 minutes to form a blend;

(e) sifting the blend obtained in step (d) through Sieve #30;

(f) blending the sifted blend of step (e) for about 13 minutes at 21 rpm in a V-blender;

(g) sifting a remaining portion of colloidal silicon dioxide through Sieve #20 using a suitable portion of the step (f) blend to aid in mixing and screening;

(h) blending the sifted second portion of colloidal silicon dioxide of step (g) blend in a V-blender of step (f) for about 7 minutes at 21 rpm;

(i) sifting calcium stearate through sieve #40 using a portion of the step (h) blend to aid in mixing and screening;

(j) blending the calcium stearate with the blend from step (i) in a V-blender from step (h) for about 7 minutes at 21 rpm to obtain a final mix blend;

(k) compressing the final-mix blend into tablets using direct compression tablet press; and

(l) packaging the tablets into high-density polyethylene (HDPE) containers.

In other embodiments, the present invention provides a composition prepared by a process comprising a milling process which provides chlorthalidone having a specific surface area from about 0.25 m²/g to about 1 m²/g.

In some embodiments, the present invention provides a method of treating hypertension in a mammalian subject comprising administering a chlorthalidone tablet to said mammalian subject, wherein the tablet is unscored and administered as a whole without splitting.

In certain embodiments, the present invention provides a method of treating hypertension in a mammalian subject, comprising administering a chlorthalidone tablet as described herein to said mammalian subject, wherein the tablet substantially disintegrates in dissolution media in less than about 30 seconds.

In other embodiments, the present invention provides a method of treating hypertension in a mammalian patient comprising administering a chlorthalidone tablet as described herein, wherein the tablet comprises chlorthalidone in amount of about 12.5 mg.

In some embodiments, the present invention provides a method of treating, reducing, preventing or ameliorating a symptom associated with hypertension in a subject in need thereof, comprising administering to said subject in need thereof, an effective amount of a solid oral composition comprising:

(i) chlorthalidone, or a pharmaceutically acceptable salt thereof, having a Sauter's mean diameter ($D_{3,2}$) of from about 8 μm to about 14 μm; and (ii) a pharmaceutically acceptable carrier comprising an excipient selected from: a diluent; a disintegrant; a glidant; a lubricant; and a combination of two or more thereof;

wherein the composition releases not less than about 58% of the chlorthalidone within 15 minutes in dissolution media having a pH of 1.2, pH 4.5, or pH 6.8;

wherein the dissolution testing is conducted in a USP Type I (basket) apparatus at 100 rpm in 500 ml of dissolution media maintained at 37±0.5° C.; and wherein the composition after storage at 25° C. and 60% relative humidity for at least about 12 months, or after storage at 40° C. and 75% relative humidity for 6 months has at least two of (a) to (c):

(a) the total impurities in an amount that does not exceed about 1%;

(b) impurity B in an amount that does not exceed about 0.5%;

(c) chlorthalidone ethyl ether impurity in an amount that does not exceed about 0.1%;

wherein the impurity concentration is calculated based on the weight of chlorthalidone.

Some embodiments of the present invention provide a method of treating hypertension in a patient in need thereof, comprising: administering a solid oral composition comprising chlorthalidone, or a pharmaceutically acceptable salt thereof, wherein when the composition is stored at 25° C. and 60% relative humidity for at least 24 months or at least 36 months has at least two of (a) to (c):

(a) the total impurities in an amount that does not exceed about 1%;

(b) impurity B in an amount that does not exceed about 0.5%;

(c) chlorthalidone ethyl ether impurity in an amount that does not exceed about 0.1%;

28 wherein the impurity concentration are calculated based on the weight of chlorthalidone.

Any embodiments specifically and explicitly recited herein may form the basis of a disclaimer either alone or in combination with one or more further embodiments. Hereinafter, the invention will be more specifically described by way of Examples. The examples are not intended to limit the scope of the invention and are merely used as illustrations.

EXAMPLES

Example 1: Exemplary Formula for Chlorthalidone Tablets

Described in Table 1 (below) is an exemplary formula for chlorthalidone tablets, 12.5 mg.

TABLE 1

| S. No. | Ingredients | Function | Quantity/ Tablet (mg) | Percentage Composition (w/w) |
|---|---|---|---|---|
| 1 | Chlorthalidone, USP | Active ingredient | 12.500 | 35.71 |
| 2 | Microcrystalline Cellulose | Diluent | 14.075 | 40.21 |
| 3 | Sodium Starch Glycolate | Disintegrant | 2.500 | 7.14 |
| 4 | Pregelatinized Starch | Disintegrant | 5.250 | 15.00 |
| 5 | Colloidal Silicon Dioxide | Glidant | 0.350 | 1 |
| 6 | Calcium Stearate | Lubricant | 0.325 | 0.93 |
| | Total weight | | 35 mg | 100% |

Example 2: Process for Manufacturing Chlorthalidone Tablets

Chlorthalidone tablets, 12.5 mg were manufactured by using a direct compression process which involved unit operations such as dispensing/weighing, milling of drug substance, sifting, blending and compression. A summary of the manufacturing process is described below:

Step 1 (Dispensing/Weighing): Each material was weighed properly in a tared polyethylene lined container. Each container was closed properly and was labeled appropriately.

Step 2 (Milling): Chlorthalidone was passed separately through Fitz-mill using a 0.020" screen, with knives in reverse position, at a high speed of approximately 4700 rpm at a feed rate of approximately 150 g/minute. The material was re-milled under the same conditions, and the milled material was collected in suitable, double polyethylene-lined containers.

Step 3 (Sifting): sodium starch glycolate, portion of colloidal silicon dioxide, and pregelatinized starch, was screened through sieve #20 which was collected in a suitable double polyethylene lined bag.

Step 4 (Premixing): microcrystalline cellulose was loaded into in a covered and closed 2 cu.ft. V-blender and was blended for 4 minutes at 21 rpm.

Step 5: milled chlorthalidone, and sifted materials from Step 3 were transferred into the 2 cu.ft. V-blender of Step 4. the mixture was blended further for 4 minutes at 21 rpm. The blend was unloaded into clean, double polyethylene bags lined containers.

Step 6 (Sifting of Pre-mix Blend): the blend from Step 5 was screened through Sieve #30 and collected in a clean double polyethylene lined container.

Step 7 (Blending): the Step 6 materials were loaded back into a 2 cu. ft. V-blender which was blended for 13 minutes at 21 rpm.

Step 8: the remaining portion of colloidal silicon dioxide was screened through sieve #20 by using a small quantity of the above Step 7 blend from the blender to facilitate mixing and screening.

Step 9: the Step 8 materials were loaded into 2 cu. ft. V-blender of Step 7. The content of mixture was blended for 7 minutes at 21 rpm.

Step 10: calcium stearate was screened through sieve #40 by using small quantity of the Step 9 blend from the blender to facilitate mixing and screening. The material was collected into a suitable container lined with double polyethylene bags.

Step 11 (Final-mix Blending): the sifted materials from Step 10 were loaded into a 2 cu. ft. V-blender and the mixture was blended for 7 minutes at 21 rpm. The final-mix blend was unloaded into a suitable clean, tarred, labeled container lined with clean double polyethylene bags.

Step 12 (Direct Compression): the final-mix blend was directly compressed using tablet compression machine.

Example 3: Sauter's Mean Diameter & Particle Size Distribution of Chlorthalidone Tablets Procedure: The key particle parameters such as particle size distribution ($D_{10}$, $D_{50}$, $D_{90}$), the Sauter's mean diameter ($D_{3,2}$), the volume-weighted mean diameter ($D_{4,3}$) and the specific surface area of both milled and unmilled chlorthalidone, API (active pharmaceutical ingredient) batches were measured using Malvern particle size analyzer. The milled API was obtained as per the process of milling described in Example 2 (above). One spoon of the sample API was transferred into the hopper, and the lid was closed. The instrument was set up as shown below in Table 2.

TABLE 2

| | Malvern Particle Size Analyzer Instrument Conditions | |
|---|---|---|
| 1 | Sample handling unit | Aero S |
| 2 | Particle type | Non-spherical |
| 3 | Material properties | Particle Refractive Index: 1.694 |
| | | Particle Absorption: 0.000 |
| | | Particle Density: 1.60 g/cm³ |
| 4 | Dispersant properties | Dispersant name: Dry dispersion |
| | | Dispersant Refractive index: 1.000 |
| 5 | Measurement duration | |
| | Background measurement duration (Red) | 20 seconds |
| | Sample measurement duration (Red) | 10 seconds |
| 6 | Measurement sequence | |
| | Aliquot | 1 |
| | No. of Measurements: | 1 |
| | Delay between measurements | 0 seconds |
| | Pre alignment delay | 0 seconds |
| 7 | Measurement obscuration settings | |
| | Auto start measurement | Yes |
| | Obscuration low limit | 0.1% |
| | Obscuration high limit | 10.00% |
| | Enable obscuration filtering | Yes |
| 8 | Accessory control settings | |
| | Feed rate | 35% |
| | Air pressure | 1.0 bar |
| | Venturi type | High energy venture disperser |
| | Tray type | General purpose tray (with hopper) |
| | Hopper gap (mm) | 3.00 mm |
| 9 | Analysis settings | |
| | Analysis model | General purpose |
| | Analysis sensitivity | Normal |
| | Fine particle mode | Yes |
| 10 | Results settings | |
| | Result units | Volume |
| | Range | No |
| 11 | Averaging | |
| | Create average | No |

The instrument was initiated, and the readings were measured for background, and the sample. Particle size distribution and key parameters including Sauter's mean diameter and specific surface area for milled and unmilled chlorthalidone used for making tablet composition of 12.5 mg measured using Malvern particle size analyzer are described in Table 3 (below).

TABLE 3

| | | | | | | | | |
|---|---|---|---|---|---|---|---|---|
| | Chlorthalidone (API)-Particle Size by Malvern | | | | | | | |
| | API Lot# | | | | | | | |
| | A1000527 | | A1001520 | | A1001521 | | A1001522 | |
| | Particle density (g/cm³) | | | | | | | |
| | 1.6 | | 1.6 | | 1.6 | | 1.6 | |
| | Unmilled API | Milled API | Unmilled API | Milled API | Unmilled API | Milled API | Unmilled API | Milled API |
| D10 (μm) | 23 | 5 | 23 | 4 | 18 | 4 | 22 | 5 |
| D50 (μm) | 188 | 23 | 182 | 25 | 165 | 22 | 183 | 36 |
| D90 (μm) | 343 | 113 | 353 | 107 | 330 | 94 | 366 | 160 |
| D 3,2 (μm) Sauter's mean diameter | 47 | 10 | 46 | 10 | 41 | 9 | 46 | 13 |
| D 4,3 (μm) | 187 | 62 | 189 | 50 | 172 | 48 | 191 | 63 |
| Specific Surface Area (m²/kg) | 81 | 367 | 81 | 371 | 92 | 425 | 81 | 296 |
| Specific Surface Area (m²/g) | 0.081 | 0.367 | 0.081 | 0.371 | 0.092 | 0.425 | 0.081 | 0.296 |

Example 4: Multimedia Dissolution Profile of Chlorthalidone Tablets

The chlorthalidone tablets (12.5 mg) were prepared in two separate batches. The batch number #382FD-01-02 was prepared without milling chlorthalidone (Un-milled API), whereas batch number A1004334 was prepared with milled API as per the process followed in Example 2. The dissolution of chlorthalidone tablets at different pH (e.g., pH 1.2, pH 4.5 and pH 6.8) was carried out as per the USP Apparatus I (Basket), 100 rpm in 500 ml of dissolution media. The process for each dissolution media is described as below:

(a) Preparation of Hydrochloric Acid dissolution media Buffer (0.1N HCl, 1.2 pH)

Transfer 8.5 mL of Concentrated Hydrochloric acid into a 1000 mL volumetric flask, dilute to volume with water and mix well.

(b) Preparation of Acetate buffer as dissolution media (pH 4.5)

Weigh about 2.99 g of sodium acetate trihydrate $(NaC_2H_3O_2 \cdot 3H_2O)$ into a 1000 mL volumetric flask, and add 14 mL of 2N acetic acid[1], make volume with water and mix well.

(c) Preparation of Phosphate Buffer as dissolution media (pH 6.8)

Transfer 250 mL of 0.2M potassium phosphate[2] monobasic $(KH_2PO_4)$ into a 1000 mL volumetric flask and add 112 mL of 0.2M sodium hydroxide[3], make up to volume with water and mix well.

[1]Preparation of 2 N Acetic Acid: Add 116 mL (120.10 g in 1000 mL) of glacial acetic acid to sufficient water to make 1000 mL, mix well.

[2]Preparation of 0.2 M Monobasic Potassium Phosphate: Dissolve 27.22 g of potassium phosphate monobasic $(KH_2PO_4)$ in 1000 ml of water, mix well.

[3]Preparation of 0.2M Sodium hydroxide: Dissolve 8 g of sodium hydroxide in 1000 mL of water, mix well.

(d) Dissolution Parameters

TABLE 4

| Dissolution Media: | 0.1N HCl, Acetate Buffer (pH 4.5) and Phosphate Buffer (pH 6.8 |
| Volume: | 500 mL |
| Dissolution Apparatus | USP I (Basket) |
| RPM | 100 rpm |
| Temperature: | 37 ± 0.5° C. |
| Profile Time Points | 15, 30, 45 and 60 min |

(e) UV-VIS Spectrophotometry Conditions

TABLE 5

| Wavelength | 275 nm |
| Cuvette path length | 1 cm |

(f) Preparation of Diluent: use dissolution media as diluent.

(g) Preparation of Standard Solution: accurately weigh and transfer about 27 mg of chlorthalidone USP reference/in-house working standard into a 100 mL volumetric flask, 70 mL of methanol to it, sonicate 5 min to dissolve, cool to room temperature, dilute to volume with methanol and mix well. Pipette 5.0 mL of above solution into a 100 mL volumetric flask, dilute to volume with diluent and mix well. Filter through 0.45μ PVDF filter by discarding at least 2 mL of the filtrate. (Concentration of Chlorthalidone is ~13.5 μg/mL)

(h) Preparation of sample solution: weigh each tablet and record the weights. Fill the vessels of each dissolution bath with 900 mL of dissolution media and allow them to equilibrate to 37° C.±0.5° C. Load the dosage unit into each vessel and start the test. Make sure there are no air bubbles on the outer surface of the tablets, as they can interfere with the dissolution. At the specified time interval, withdraw about 10 mL of the sample solution from each dissolution vessel. Filter through 0.45μ PVDF filter by discarding at least 2 mL of the filtrate.

(i) Evaluation of system suitability: measure UV absorbance of the Diluent (1 solution), standard preparation five times by the UV-VIS spectrophotometer.

The system is suitable if:

The RSD for five replicate readings of Chlorthalidone of standard solution is NMT 2.0%

Procedure: measure UV absorbance of the following sequence and record the values:

TABLE 6

| S. No. | Sample ID | No. of Injections |
| --- | --- | --- |
| 1 | Diluent | 1 |
| 2 | Standard | 5 |
| 3 | Test Sample | 1 |

(j) Calculation:

For 12.5 mg dosage:

$$\% \text{ Dissolution} = \left(\frac{Ru}{Rs}\right) \times \left(\frac{Ws \text{ (mg)}}{100 \text{ (mL)}}\right) \times \left(\frac{5 \text{ (mL)}}{100 \text{ (mL)}}\right) \times \left(\frac{900 \text{ mL}}{1}\right) \times \left(\frac{P \text{ (\%)}}{100}\right) \times \left(\frac{100}{LC \text{ (mg)}}\right)$$

Where:

Ru: UV Absorbance of Chlorthalidone in the sample solution

Rs: Average UV Absorbance of Chlorthalidone in the standard solution

Ws: Weight of the Chlorthalidone USP Reference standard (mg)

P: Potency of the Chlorthalidone USP Standard (% w/w, on as is basis)

LC: Label Claim of Chlorthalidone, 12.5 (mg)

Table 7 (below) describes the dissolution profile of chlorthalidone tablets, 12.5 mg, prepared with milled and unmilled chlorthalidone API, in 0.1 N hydrochloric acid dissolution media.

TABLE 7

| | Dissolution media 0.1N HCl, 500 ml, pH 1.2, USP apparatus I (basket) Batch# | | | | |
| --- | --- | --- | --- | --- | --- |
| | #382FD-01-02 (Un-milled API) | | #A1004334 (Milled API) | | % increase |
| Time in Minutes | % Drug Dissolved | % RSD | % Drug Dissolved | % RSD | in dissolution unmilled vs milled |
| 15 | 45 | 4.5 | 69 | 4.0 | 53.30 |
| 30 | 61 | 5.0 | 91 | 3.3 | 49.18 |
| 45 | 69 | 4.5 | 99 | 3.3 | 43.47 |
| 60 | 73 | 4.7 | 104 | 4.2 | 42.46 |

Table 8 (below) describes the dissolution profile of chlorthalidone tablets USP, 12.5 mg, prepared with milled and unmilled chlorthalidone API, in 4.5 acetate buffer dissolution media.

US 12,667,554 B1

33

TABLE 8

Dissolution media
Acetate buffer, 500 ml, pH 4.5, USP apparatus I (basket)
Batch#

| Time in Minutes | #382FD-01-02 (Un-milled API) | | #A1004334 (Milled API) | | % increase |
| | % Drug Dissolved | % RSD | % Drug Dissolved | % RSD | in dissolution unmilled vs milled |
| --- | --- | --- | --- | --- | --- |
| 15 | 43 | 8.7 | 62 | 4.0 | 44.18 |
| 30 | 58 | 8.5 | 82 | 2.7 | 41.37 |
| 45 | 66 | 8.8 | 89 | 2.1 | 34.84 |
| 60 | 71 | 8.6 | 92 | 2.2 | 29.57 |

Table 9 (below) describes the dissolution profile of chlorthalidone tablets, 12.5 mg, prepared with milled and unmilled chlorthalidone API, in 6.8 phosphate buffer dissolution media.

TABLE 9

Dissolution media
Phosphate buffer, 500 ml, pH 6.8, USP apparatus I (basket)
Batch#

| Time in Minutes | #382FD-01-02 ((Un-milled API) | | #A1004334 (Milled API) | | % increase |
| | % Drug Dissolved | % RSD | % Drug Dissolved | % RSD | in dissolution unmilled vs milled |
| --- | --- | --- | --- | --- | --- |
| 15 | 51 | 3.0 | 68 | 3.9 | 33.33 |
| 30 | 64 | 4.2 | 84 | 3.6 | 31.25 |
| 45 | 73 | 3.0 | 91 | 6.0 | 24.65 |
| 60 | 78 | 3.5 | 93 | 6.3 | 19.23 |

Example 5: Disintegration Study of Chlorthalidone Tablets, 12.5 mg

One (1) dosage unit was placed in each of the 6 tubes of the basket rack assembly. The apparatus was operated, using water as the immersion fluid, maintained at 37±2° C. All of the tablets should disintegrate completely. The disintegration time (aka disintegration profile) was recorded for each tablet individually and reported as shown in below Table 10.

TABLE 10

| | Chlorthalidone Tablets, 12.5 mg | | |
| Test | Batch# A1003575 | Batch# A1004333 | Batch# A1004334 |
| --- | --- | --- | --- |
| Disintegration Time | 10-11 seconds | 13-17 seconds | 11-12 seconds |

Example 6: Long-Term Stability at 25° C. And 60% Relative Humidity

Exemplary 12.5 mg chlorthalidone tablets, manufactured in accordance with the processes described in Example 2, were subjected to storage stability testing at 25° C., 60% relative humidity (RH) for 12 months, 24 months and 36 months. The assay of drug as well as content of known and unknown impurities was analyzed initially and after given storage time and condition. The content of total impurities and individual impurities were analyzed by high-performance liquid chromatography (HPLC). The results are summarized below in Table 11.

34

TABLE 11

Chlorthalidone Tablets, 12.5 mg (Batch# A1004334)
Conditions: 25° C., 60% RH

| Test | Specification | Time in Months | | | |
| | | 0 (initial) | 12 | 24 | 36 |
| --- | --- | --- | --- | --- | --- |
| Water Content by K.F. | | 2.5 | 2.9 | 3,0 | 2.3 |
| Assay (By HPLC) | | 101.8 | 100.5 | 101.1 | 99.2 |
| Related Substances (By HPLC) w/w % | Chlorthalidone Related Compound A (EP Impurity B) | 0.3 | 0.3 | 0.3 | 0.3 |
| | Chlorthalidone ethyl ether impurity | 0.08 | 0.07 | 0.07 | 0.07 |
| | Single unknown Impurity | 0.07 | 0.05 | 0.05 | 0.06 |
| | Total Impurities | 0.7 | 0.7 | 0.6 | 0.6 |

The analytical results of a long-term stability study of exemplary chlorthalidone tablets of the present invention (12.5 mg) were found to be satisfactory across all physical and chemical parameters as evident above, when stored at 25° C. and 60% RH over a period of 12 months, 24 months and 36 months.

Example 7: Accelerated Stability Testing at 40° C. and 75% RH

Exemplary 12.5 mg chlorthalidone tablets, manufactured in accordance with the processes described in Example 2, were subjected to storage stability testing at 40° C. and 75% RH for 6 months. The assay of drug as well as content of known and unknown impurities was analyzed initially and after given storage time and condition. The content of total impurities and individual impurities were analyzed by HPLC. The results are summarized below in Table 12.

TABLE 12

Chlorthalidone Tablets, 12.5 mg (Batch# A1004334)
Conditions: 40° C., 75% RH

| Test | Specification | Time in Months | | | |
| | | 0 | 1 | 3 | 6 |
| --- | --- | --- | --- | --- | --- |
| Water Content by K.F. | | 2.5 | 3.5 | 2.9 | 2.7 |
| Assay (By HPLC) | | 101.8 | 102.7 | 102.0 | 101.5 |
| Related Substances (By HPLC) w/w % | Chlorthalidone Related Compound A (EP Impurity B) | 0.3 | 0.3 | 0.3 | 0.3 |
| | Chlorthalidone ethyl ether impurity | 0.08 | 0.05 | 0.05 | 0.07 |
| | Single unknown Impurity | 0.07 | 0.06 | 0.06 | 0.06 |
| | Total Impurities | 0.7 | 0.6 | 0.6 | 0.6 |

The analytical results of the long-term stability study of exemplary chlorthalidone tablets of the present invention (12.5 mg) were found to be satisfactory across all physical and chemical parameters as evident above, when stored at accelerated condition of 40° C. and 75% RH over a period of 1 month, 3 months and 6 months.

What is claimed is:

1. A solid oral composition comprising:

chlorthalidone, or a pharmaceutically acceptable salt thereof, having:

a Sauter's mean diameter ($D_{3,2}$) of from 8 μm to 14 μm; and a specific surface area of from 0.25 $m^2$/gram to 0.5 $m^2$/gram; and a pharmaceutically acceptable carrier;

wherein the pharmaceutically acceptable carrier comprises:

about 40% w/w of microcrystalline cellulose;

about 7% w/w sodium starch glycolate;

about 15% w/w pregelatinized starch;

about 1% w/w of colloidal silicon dioxide; and about 0.9% w/w of calcium stearate;

wherein the solid oral composition releases not less than 58% of chlorthalidone within 15 minutes in dissolution media having a pH of 1.2, 4.5, or 6.8; and wherein the dissolution testing is conducted in a USP Type I basket apparatus at 100 rpm in 500 ml of dissolution media maintained at 37±0.5° C.

2. The solid oral composition according to claim 1, wherein the pharmaceutically acceptable carrier comprises:

40.21% w/w of microcrystalline cellulose;

7.14% w/w of sodium starch glycolate;

15% w/w of pregelatinized starch;

1% w/w of colloidal silicon dioxide; and 0.93% w/w of calcium stearate.

3. The solid oral composition according to claim 1, wherein the solid oral composition is in the form of a tablet.

4. The solid oral composition according to claim 3, wherein the tablet substantially disintegrates in the dissolution media in less than 30 seconds.

5. The solid oral composition according to claim 3, wherein the tablet comprises 12.5 mg of chlorthalidone, or a pharmaceutically acceptable salt thereof.

6. The solid oral composition according to claim 3, wherein the tablet is unscored and administered to the subject without splitting.

7. The solid oral composition according to claim 1, wherein the solid oral composition releases not less than 80% of chlorthalidone, or a pharmaceutically acceptable salt thereof, within 30 minutes.

8. The solid oral composition according to claim 1, wherein the solid oral composition releases not less than 84% of chlorthalidone, or a pharmaceutically acceptable salt thereof, within 45 minutes.

9. The solid oral composition according to claim 1, wherein the solid oral composition releases not less than 90% of chlorthalidone, or a pharmaceutically acceptable salt thereof, within 60 minutes.

10. The solid oral composition according to claim 1, wherein after storage at 25° C. and 60% relative humidity for at least 12 months, or after storage at 40° C. and 75% relative humidity for 6 months, the solid oral composition has:

(a) total impurities in an amount that does not exceed about 1%; and (b) chlorthalidone ethyl ether impurity in an amount that does not exceed about 0.1%;

wherein the impurity concentrations are calculated based on the weight of chlorthalidone.

11. The solid oral composition according to claim 1, wherein after storage at 25° C. and 60% relative humidity for at least 24 months, the solid oral composition has:

(a) total impurities in an amount that does not exceed about 1%; and (b) chlorthalidone ethyl ether impurity in an amount that does not exceed about 0.1%;

wherein the impurity concentrations are calculated based on the weight of chlorthalidone.

12. The solid oral composition according to claim 1, wherein after storage at 25° C. and 60% relative humidity for at least 36 months, the solid oral composition has:

(a) total impurities in an amount that does not exceed about 1%; and (b) chlorthalidone ethyl ether impurity in an amount that does not exceed about 0.1%;

wherein the impurity concentrations are calculated based on the weight of chlorthalidone.

* * * * *